US009410137B2

(12) United States Patent
Camire

(10) Patent No.: US 9,410,137 B2
(45) Date of Patent: Aug. 9, 2016

(54) COMPOSITIONS AND METHODS FOR MODULATING HEMOSTASIS

(71) Applicant: The Children's Hospital of Philadelphia, Philadelphia, PA (US)

(72) Inventor: Rodney M. Camire, Sicklerville, NJ (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 482 days.

(21) Appl. No.: 13/726,187

(22) Filed: Dec. 23, 2012

(65) Prior Publication Data
US 2014/0120155 A1 May 1, 2014

Related U.S. Application Data

(62) Division of application No. 12/093,783, filed as application No. PCT/US2006/060927 on Nov. 15, 2006, now Pat. No. 8,383,386.

(60) Provisional application No. 60/736,680, filed on Nov. 15, 2005.

(51) Int. Cl.
*C12N 9/64* (2006.01)
*A61K 38/48* (2006.01)

(52) U.S. Cl.
CPC .......... *C12N 9/6432* (2013.01); *A61K 38/4846* (2013.01); *C12N 9/647* (2013.01); *C12Y 304/21006* (2013.01)

(58) Field of Classification Search
CPC ..................... C12Y 304/21006; C12N 9/6432; A61K 38/4846
USPC ......................................... 435/212; 530/384
See application file for complete search history.

(56) References Cited

U.S. PATENT DOCUMENTS

| 6,958,322 | B1 | 10/2005 | Himmelspach et al. | |
| 7,220,569 | B2 | 5/2007 | Himmelspach et al. | |
| 8,436,144 | B2 * | 5/2013 | Christophe et al. | 530/381 |
| 2003/0181381 | A1 | 9/2003 | Himmelspach et al. | |

FOREIGN PATENT DOCUMENTS

| EP | 1728798 | | 12/2006 | |
| WO | 98/38317 | | 9/1998 | |
| WO | 98/38318 | | 9/1998 | |
| WO | 01/70763 | | 9/2001 | |
| WO | WO 03/035861 | * | 5/2003 | ............... C12N 9/64 |
| WO | 2004/005347 | | 1/2004 | |

OTHER PUBLICATIONS

Maekawa et al, Biochemistry 32:6146-6151, 1993.*
Wolf, D.L., et al. "Design of Constructs for the Expression of Biologically Active Recombinant Human Factors X and Xa." J Biol Chem. Jul. 25, 1991;266(21)13726-13730.
Friedrich, R., et al. "Staphylocoagulase is a prototype for the mechanism of cofactor0induced zymogen activation." Nature, 425: 535-539 (Oct. 2, 2003).
"SEQ ID No. 2 mi file" uploaded as partial result from PTO search file entitled "Sequence Search—20070801_095501_pct-us06-60—20070801_095501_pct-us06-60927-2-.mi" in order to demonstrate homology of claimed sequence to previously published sequence.
Sun, T., et al. "Vitamin K epoxide reductase significantly improves carboxylation in a cell line overexpressing factor X." Blood, 106(12):3811-3815 (Aug. 4, 2005).
Camire, R., et al. "Enhanced gamma-carboxylation of recombinant factor X using a chimeric construct containing the prothromcin propeptide." Biochemistry, 39(46): 14322-14329 (Nov. 21, 2000).
Camire, R. "Prothrombinase assembly and S1 site occupation restore the catalytic activity of FXa impaired by mutation at the sodium-binding site." Journal of Biological Chemistry, 277(40):37863-37870 (Oct. 4, 2002).
Hedstrom, L, et al. "Hydrophobic interactions control zymogen activation in the trypsin family of serine proteases." Biochemistry, 35(14): 4515-4523 [Abstract] (1996).
Toso, R., et al. "Factor VII mutant V154G models a zymogen-like form of factor VIIa." The Biochemical Journal, 369 (3):563-471 (Feb. 1, 2003).
Toso, R., et al. "Factor VII variants as tools to study Factor VIIa salt bridge formation." Database Biosis. Biosciences, Information Service, Philadelphia, PA & Blood, 98(11):526a (Nov. 16, 2001) [Abstract].
Toso, R., et al. "Alteration of the factor X zymogen to protease transition provides evidence for allosteric linkage between the S1 and FVa binding sites." Blood, 106(11):13A (Nov. 16, 2005).
Toso, R., et al. "The conformational switch from the factor X zymogen to protease state mediates exosite expression and prothrombinase assembly." Journal of Biological Chemistry, 283(17):18627-18635 (Jul. 2008).
Strandberg, L., et al. "Variants of tissue-type plasminogen activator with substantially enhanced response and selectivity toward fibrin co-factors." J Biol Chem. Oct. 6, 1995;270(40):23444-9.
Sziegoleit. GenBank CAA74031.1; 1997.
Wells, J.A. "Additivity of mutational effects in proteins." Biochemistry. Sep. 18, 1990;29(37):8509-17.
Ngo, J.T., et al. "Computational Complexity, Protein Structure Prediction and the Levinthal Paradox." In Peptide Hormones (J.A. Parsons, ed.) University Park Press. 1994:492-495.
Guo, H.H., et al. "Protein tolerance to random amino acid change." Proc Natl Acad Sci U S A. Jun. 22, 2004;101(25):9205-10. Epub Jun. 14, 2004.
Hult, K., et al. "Engineered enzymes for improved organic synthesis." Curr Opin Biotechnol. Aug. 2003;14(4):395-400.
Rudinger, J. "Characteristics of the amino acids as components of a peptide hormone sequence." In Peptide Hormones (J.A. Parsons, ed.) University Park Press.1976:1-7.
Holt, K. Q5JVE7, GI:74742424. May 2005.
Rudolph, A.E., et al. "Expression, purification, and characterization of recombinant human factor X." Protein Expr Purif. Aug. 1997;10(3):373-8.
Bianchini, E.P., et al. "Mapping of the catalytic groove preferences of factor Xa reveals an inadequate selectivity for its macromolecule substrates." J Biol Chem. Jun. 7, 2002;277(23):20527-34. Epub Mar. 29, 2002.
Khan, A.R., et al. "Molecular mechanisms for the conversion of zymogens to active proteolytic enzymes." Protein Science. 1998;7:815-836.

* cited by examiner

*Primary Examiner* — Kevin Hill
(74) *Attorney, Agent, or Firm* — Kathleen D. Rigaut; Dann, Dorfman, Herell & Skillman

(57) ABSTRACT

Factor Xa variants and methods of use thereof are disclosed.

20 Claims, 11 Drawing Sheets

Figure 5A

```
     MetGlyArg ProLeuHisLeu ValLeuLeu SerAlaSer LeuAlaGlyLeu LeuLeuLeu GlyGluSer
981  ATGGGGCGC CCACTGCACC TGGTCCTGCT CAGTGCCTCC CTGGCTGGCC TCCTCCTGCT CGGGGAAAGT
     TACCCCGCG GGTGACGTGG AGCAAGGACGA GTCACGGAGG GACCGACCGG AGGACGACGA GCCCCTTTCA
                                                                        +1 Start
     LeuPheIleArg ArgGluGln AlaAsnAsn IleLeuAlaArg ValArgArg AlaAsnSer PheLeuGluGlu
1051 CTGTTCATCC GCAGGGAGCA GGCCAACAAC ATCCTGGCGA GGGTCAGGAG GGCCAATTCC TTTCTTGAAG
     GACAAGTAGG CGTCCCTCGT CCGGTTGTTG TAGGACCGCT CCCAGTCCTC CCGGTTAAGG AAAGAACTTC MetLysLys GlyHisLeu GluArgGluCys MetGluGlu ThrCysSer TyrGluGluAla ArgGluVal.
1121 AGATGAAGAA AGGACACCTC GAAAGAGAGT GCATGGAAGA GACCTGCTCA TACGAAGAGG CCCGCGAGGT
     TCTACTTCTT TCCTGTGGAG CTTTCTCTCA CGTACCTTCT CTGGACGAGT ATGCTTCTCC GGGCGCTCCA .PheGluAsp SerAspLysThr AsnGluPhe TrpAsnLys TyrLysAspGly AspGlnCys GluThrSer
1191 CTTTGAGGAC AGCGACAAGA CGAATGAATT CTGGAATAAA TACAAAGATG GCGACCAGTG TGAGACCAGT
     GAAACTCCTG TCGCTGTTCT GCTTACTTAA GACCTTATTT ATGTTTCTAC CGCTGGTCAC ACTCTGGTCA ProCysGlnAsn GlnGlyLys CysLysAsp GlyLeuGlyGlu TyrThrCys ThrCysLeu GluGlyPheGlu.
1261 CCTTGCCAGA ACCAGGGCAA ATGTAAAGAC GGCCTCGGGG AATACACCTG CACCTGTTTA GAAGGATTCG
     GGAACGGTCT TGGTCCCGTT TACATTTCTG CCGGAGCCCC TTATGTGGAC GTGGACAAAT CTTCCTAAGC .GlyLysAsp CysGluLeu PheThrArgLys LeuCysSer LeuAspAsn GlyAspCysAsp GlnPheCys.
1331 AAGGCAAAAA CTGTGAATTA TTCACACGGA AGCTCTGCAG CCTGGACAAC GGGGACTGTG ACCAGTTCTG
     TTCCGTTTTT GACACTTAAT AAGTGTGCCT TCGAGACGTC GGACCTGTTG CCCCTGACAC TGGTCAAGAC .HisGluGlu GlnAsnSerVal ValCysSer CysAlaArg GlyTyrThrLeu AlaAspAsn GlyLysAla
```

Figure 5B
1401 CCACGAGGAA CAGAACTCTG TGGTGTGCTC CTGCGCCCGC GGGTACACCC TGGCTGACAA CGGCAAGGCC
     GGTGCTCCTT GTCTTGAGAC ACCACACGAG GACGCGGGCG CCCATGTGGG ACCGACTGTT GCCGTTCCGG
     CysIleProThr GlyProTyr ProCysGly LysGlnThrLeu GluArgArg LysProTyr ValAlaGlnAla.

1471 TGCATTCCCA CAGGCCCTA CCCCGTGTGG AAACAGACCC TGGAACCCAG GAAGAGGTCA GTGGCCCAGG
     ACGTAAGGGT GTCCGGGAT GGGGCACACC TTTGTCTGGG ACCTTGCGTC CTTCTCCAGT CACCGGGTCC
     ..ThrSerSer SerGlyGlu AlaProAspSer IleThrTrp LysProTyr AspAlaAlaAsp LeuAspPro.

1541 CCACCAGCAG CAGCGGGGAG GCCCCTGACA GCATCACATG GAAGCCATAT GATGCAGCCG ACCTGGACCC
     GGTGGTCGTC GTCGCCCCTC CGGGGACTGT CGTAGTGTAC CTTCGGTATA CTACGTCGGC TGGACCTGGG
     .ThrGluAsn ProPheAspLeu LeuAspPhe AsnGlnThr GlnProGluArg GlyAspAsn AsnLeuThr

1611 CACCGAGAAC CCCTTCGACC TGCTTGACTT CAACCAGACG CAGCCCTGAGA GGGGCGACAA CAACCTCACG
     GTGGCTCTTG GGGAAGCTGG ACGAACTGAA GTTGGTCTGC GTCGGGACTCT CCCCGCTGTT GTTGGAGTGC
     15 16 17 18 19
     ArgIleValGly GlyGlnGlu CysLysAsp GlyGluPro TrpGlnAla LeuLeuIle AsnGluGluAsn.

1681 CGTATCGTGG GAGGCCAGGA ATGCAAGGAC GGGGAGTGTC CCTGGCAGGC CCTGCTCATC AATGAGGAAA
     GCATAGCACC CTCCGGTCCT TACGTTCCTG CCCCTCACAG GGACCGTCCG GGACGAGTAG TTACTCCTTT
     ..GlyGlyPhe CysGlyGly ThrIleLeuSer GluPheTyr IleLeuThr AlaAlaHisCys LeuTyrGln.

1751 ACGAGGGTTT CTGTGGTGGA ACTATTCTGA GCCAGTTCTA CATCCTAACG GCAGCCCACT GTCTCTACCA
     TGCTCCCAAA GACACCACCT TGATAAGACT CGGTCAAGAT GTAGGATTGC CGTCGGGTGA CAGAGATGGT
     .AlaLysArg PheLysValArg ValGlyAsp ArgAsnThr GluGlnGluGlu GlyGlyGlu AlaValHis

1821 AGCCAAGAGA TTCAAGGTGA GGTAGGGTGA CCGGAACACG GAGCAGGAGG AGGGGGTGA GGCGGTGCAC
     TCGGTTCTCT AAGTTCCACT CCATCCCACT GGCCTTGTGC CTCGTCCTCC CTCCCCACT CCGCCACGTG
     GluValGluVal ValIleLys HisAsnArg PheThrLysGlu PheAspIle AlaValLeuArg.

Figure 5C

```
1891  GAGGTGGAGG TGGTCATCAA GCACAACCGG TTCACAAAGG AGACCTATGA CTTCGACATC GCCGTGCTCC
      CTCCACCTCC ACCAGTAGTT CGTGTTGGCC AAGTGTTTCC TCTGGATACT GAAGCTGTAG CGGCACGAGG
      ..LeuLysThr ProIleThr PheArgMetAsn ValAlaPro TyrAlaCysLeu ProGluArgAsp TrpAlaGlu.

1961  GGCTCAAGAC CCCCATCACC TTCCGCATGA AGTGGGGCC TGCCTGCCTC CCGGAGCGTG ACTGGGCCGA
      CCGAGTTCTG GGGGTAGTGG AAGGCGTACT TCACCCCGG ACGGACGGAG GGGCTCGCAC TGACCCGGCT
      .SerThrLeu MetThrGlnLys ThrGlyIle ValSerGly PheGlyArgThr HisGluLys GlyArgGln

2031  GTCCACGCTG ATGACGGCAGA AGACGGGGAT TGTGAGCGGC TTCGGGGCCA CCCACGAGAA GGGCCCGGCAG
      CAGGTGCGAC TACTGCGTCT TCTGCCCCTA ACACTCGCCG AAGCCCGCGT GGGTGTCTTT CCCGGGCCGTC

SerThrArgLeu LysMetLeu GluValPro TyrValAspArg AsnSerCys LysLeuSer SerSerPheIle.

2101  TCCACCAGGC TCAAGATGCT GGAGGTGCCC TACGTGGACC AGGACACCAA GCAGGAGGAT GCCTGCCAGG GGGACAGCGG
      AGGTGGTCCG AGTTCTACGA CCTCCACGGG ATGCACCTGG CGTTGTGGTT CGTCCTCCTA CGGACGGTCC CCCTGTCGCC
                                                                                   194
      ..IleThrGln AsnMetPhe CysAlaGlyTyr AspThrLys GlnGluAsp AlaCysGlnGly AspSerGly.

2171  TCATCACCCA GAACATGTTC TGTGCCGGCT ACGACACCAA GCAACAGCTG CAAGCTGTCC AGCAGCTTCA
      AGTAGTGGGT CTTGTACAAG ACACGGCCGA TGCTGTGGTT CGTTGTCGAC GTTCGACAGG TCGTCGAAGT

2241  GGCCCCCGAC GTCACCCCGCT TCAAGGACAC CTACTTCGTG ACAGGCCATCG TCAGCTGGGG AGAGGGCTGT
      CCGGGGGCTG CAGTGGGGCGA AGTTCCTGTG GATGAAGCAC TGTCCGTAGC AGTCGACCCC TCTCCCGACA

AlaArgLysGly LysTyrGly IleTyrThr LysValThrAla PheLeuLys TrpIleAsp ArgSerMetLys.

2311  GCCCGTAAGG GGAAGTACGG GATCTACACC AAGGTCACCG CCTTCCTCAA GTGGATCGAC AGGTCCATGA
      CGGGCATTCC CCTTCATGCC CTAGATGTGG TTCCAGTGGC GGAAGGAGTT CACCTAGCTG TCCAAGTACT
```

Figure 5D

```
       .ThrArgGly LeuProLys AlaLysSerHis AlaProGlu ValIleThr SerSerProLeu Lys
2381 AAACCAGGGG CTTGCCCAAG GCCAAGAGCC ATGCCCCGGA GGTCATAACG TCCTCTCCAT TAAAGTGA
     TTTGGTCCCC GAACGGGTTC CGGTTCTCGG TACGGGGCCT CCAGTATTGC AGGAGAGGTA ATTTCACT
```

COMPOSITIONS AND METHODS FOR MODULATING HEMOSTASIS

This application is a divisional application of U.S. patent application Ser. No. 12/093,783, filed Jul. 16, 2008, now U.S. Pat. No. 8,383,386, which is a the National Stage of International Patent Application No. PCT/US2006/60927 filed Nov. 15, 2006, which claims the benefit of U.S. Provisional Application No. 60/736,680 filed Nov. 15, 2005, the entire contents of each being incorporated by reference herein as though set forth in full.

Pursuant to 35 U.S.C. §202(c), it is acknowledged that the U.S. Government has certain rights in the invention described herein, which was made in part with funds from the National Institutes of Health, Grant Numbers PO1 HL-74124-01.

FIELD OF THE INVENTION

The present invention relates to the fields of medicine and hematology. More specifically, the invention provides novel coagulation Factor X/Xa agents and methods of using the same to modulate the coagulation cascade in patients in need thereof.

BACKGROUND OF THE INVENTION

Several publications and patent documents are cited throughout the specification in order to describe the state of the art to which this invention pertains. Each of these citations is incorporated herein by reference as though set forth in full.

The enzymes of coagulation are trypsin-like enzymes that belong to the S1 peptidase family of proteases that bear a chymotrypsin-like fold. The coagulation proteases contain catalytic domains that are highly homologous to each other and to the ancestral serine proteases of digestion. The structural homology/identity is so great (>70%) that residues in the catalytic domains of the coagulation enzymes are numbered according to the corresponding residues in chymotrypsinogen.

The coagulation enzymes circulate in blood as inactive precursors, zymogens, that require proteolytic cleavage for activation. The zymogens possess ~10,000-fold or less proteolytic activity when compared to the serine proteases produced following activation. Initiation of coagulation at the site of vascular damage leads to a series of reactions in which a zymogen is converted to a protease through specific proteolytic cleavage and forms the enzyme for the successive reaction. This culminates in blood cell activation and the conversion of soluble fibrinogen to insoluble fibrin and hence the formation of the clot. Excess proteases are removed by reaction with circulating protease inhibitors that act as "suicide" substrates or those that recognize the active enzymes. Thus, proteolytic activation of the coagulation zymogens is a key regulatory feature of the coagulation cascade.

Although some of the coagulation zymogens are cleaved at two or more sites in their respective activation reactions, formation of the protease requires cleavage at a single site. Cleavage at this site and its structural consequences are considered in the most facile way using the homologous numbering system based on chymotrypsinogen and the extensive structural work done with trypsinogen and trypsin. The conversion of the zymogen to serine protease requires cleavage following $Arg^{15}$ (typically the bond between $Arg^{15}$ and $Ile^{16}$; positions 234 and 235 in SEQ ID NO: 1) which typically removes an activation peptide and exposes a new N-terminus in the catalytic domain beginning with $Ile^{16}$. One example is the conversion of factor X to factor Xa (see FIGS. 1 and 2). In trypsin and factor Xa, the new N-terminal sequence begins with $Ile^{16}$-$Val^{17}$-$Gly^{18}$-$Gly^{19}$ (positions 235, 236, 237 and 238 in SEQ ID NO: 1). For other clotting enzymes, the new N-terminal sequence is a variation on the same theme. The N-terminal sequence then folds back into the catalytic domain and inserts into the N-terminal binding cleft in a sequence-specific manner which is referred to as "molecular sexuality". See FIG. 2. Accordingly, variants with alternate N-terminal sequences are not likely to undergo molecular sexuality in a comparable way. N-terminal insertion leads to the formation of a salt bridge between the $\alpha$-$NH_2$ group of $Ile^{16}$ and $Asp^{194}$ (positions 235 and 418 in SEQ ID NO: 1, respectively) in the interior of the catalytic domain. Salt bridge formation is associated with numerous changes in catalytic domain structure including: rearrangements of the so-called activation domains, shown in FIG. 3; formation of the oxyanion hole required for catalysis and the formation of a substrate binding site. These changes lead to the maturation of the active serine protease. The key contribution of sequence-specific interactions of the new N-terminus through molecular sexuality and salt bridge formation to the maturation of the active protease are evident from the following facts: bacterial proteases that do not require cleavage for activation utilize another side-chain within the catalytic domain to salt bridge with $Asp^{194}$ (position 418 in SEQ ID NO: 1); trypsinogen can be activated to a proteinase-like conformation without cleavage but with extremely high concentrations of an Ile-Val dipeptide that inserts into the cleft, albeit very inefficiently; the Val-Ile dipeptide and other variants are far less effective; additionally, there are two examples of bacterial proteins that activate coagulation zymogens in the absence of cleavage by subverting the activation mechanism via provision of their own N-terminus that inserts into the N-terminal binding cleft.

The structural changes outlined above provide a molecular explanation for the conversion of a precursor zymogen to an active serine protease. However, unlike trypsin which is fully active following cleavage at $Arg^{15}$ (position 234 in SEQ ID NO: 1), many of the coagulation enzymes act very poorly on their protein substrates. Even though they generally possess fully functional active sites and can cleave small peptidyl substrates, efficient cleavage of the biological substrate often requires a cofactor protein (FIG. 2). In these cases, the cofactor proteins increase the rate of protein substrate cleavage by several thousand fold. Although the mechanism by which the cofactor proteins function remains to be resolved, they are unlikely to function by making the protease more enzyme-like and therefore more efficient. A key point is that, with one exception, the cofactors selectively bind the protease and not the corresponding zymogen. For example, factor Xa binds with high affinity to membrane-bound FVa, whereas the zymogen factor X does not bind FVa.

Depending on the state of the patient it may be desirable to develop altered coagulation cascade proteins which possess enhanced or reduced coagulation function. It is an object of the invention to provide such proteins for use as therapeutics.

SUMMARY OF THE INVENTION

In accordance with the present invention, compositions and methods are provided for influencing regulatory sites in the FX zymogen→protease transition pathway thereby driving production of a more "zymogen-like" FXa species. The compositions and methods of the invention are effective to modulate hemostasis in patients in need thereof.

In one embodiment, a variant Factor X/Factor Xa zymogen/protease which modulates hemostasis is provided.

Preferably, the variant zymogen protease is encoded by SEQ ID NO: 2, wherein nucleotides 1684-1695 of SEQ ID NO: 2 can be any amino acid with the proviso that nucleotides 1684-1886 do not encode Val or Ala. More preferably, the variant zymogen/protease contains at least one modification in SEQ ID NO: 1 selected from the group consisting of a) Ile at position 235 in SEQ ID NO: 1 is Leu, Phe, Asp or Gly; b) Val at position 236 in SEQ ID NO: 1 is Leu, Ala, or Gly and c) Asp at position 418 in SEQ ID NO: 1 is Asn or Glu. Nucleic acids encoding the variant zymogen/proteases of the invention are also disclosed as are methods of use thereof. Such nucleotides may optionally encode an intracellular PACE/furin cleavage site.

In yet another embodiment, a nucleic acid having the sequence of SEQ ID NO: 2, wherein the nucleotides at positions 1684-1695 encode the amino acids selected from the group consisting of Leu-Val-Gly, Gly-Val-Gly, Ile-Ala-Gly, Phe-Val-Gly and Ile-Gly-Gly, said nucleic acid optionally comprising nucleotides at position 2233-2235 which encode an amino acid selected from the group consisting of Asn or Glu.

A pharmaceutical composition comprising the Factor Xa variant of the invention in a biologically compatible carrier is also provided. Another preferred aspect of the invention includes methods for the treatment of a hemostasis related disorder in a patient in need thereof comprising administration of a therapeutically effective amount of the variant Factor X/Xa zymogen/protease containing pharmaceutical compositions described herein. Such methods should have efficacy in the treatment of disorders where a pro-coagulant is needed and include, without limitation, hemophilia A and B, hemophilia A and B associated with inhibitory antibodies, coagulation factor deficiency, vitamin K epoxide reductase Cl deficiency, gamma-carboxylase deficiency, bleeding associated with trauma, injury, thrombosis, thrombocytopenia, stroke, coagulopathy, disseminated intravascular coagulation (DIC); over-anticoagulation treatment disorders, Bernard Soulier syndrome, Glanzman thromblastemia, and storage pool deficiency.

Certain zymogen/protease variants may be useful in the treatment of disorders where anti-coagulation is desired. Such disorders include, without limitation, thrombosis, thrombocytopenia, stroke, and coagulapathy.

Another aspect of the invention, includes host cells expressing the variant zymogen/proteases of the invention in order to produce large quantities thereof. Methods for isolating and purifying the zymogen protease variants are also disclosed.

BRIEF DESCRIPTION OF THE DRAWINGS

FIG. 5. Amino acid (SEQ ID NO: 1) and nucleic acid (SEQ ID NO: 2) sequences of Factor Xa. The sites and amino acid positions for desired modifications in SEQ ID NO: 1 are shown in bold.

DETAILED DESCRIPTION OF THE INVENTION

Proteolysis is an essential aspect of blood coagulation and underlies many of the mechanisms regulating normal hemostasis. Procofactors and zymogens cannot participate to any significant degree in their respective macromolecular enzymatic complexes. This indicates that proteolytic activation must result in appropriate structural changes that lead to the expression of sites which impart enzyme, substrate and cofactor binding capabilities. While procofactor and zymogen activation has been intensively studied, the relationship between proteolysis and the expression of binding sites which impart function is incompletely understood. The present invention provides model compositions and systems which elucidate the molecular mechanisms underlying the expression of macromolecular binding interactions that accompany transitions from the zymogen state.

Figure 1:
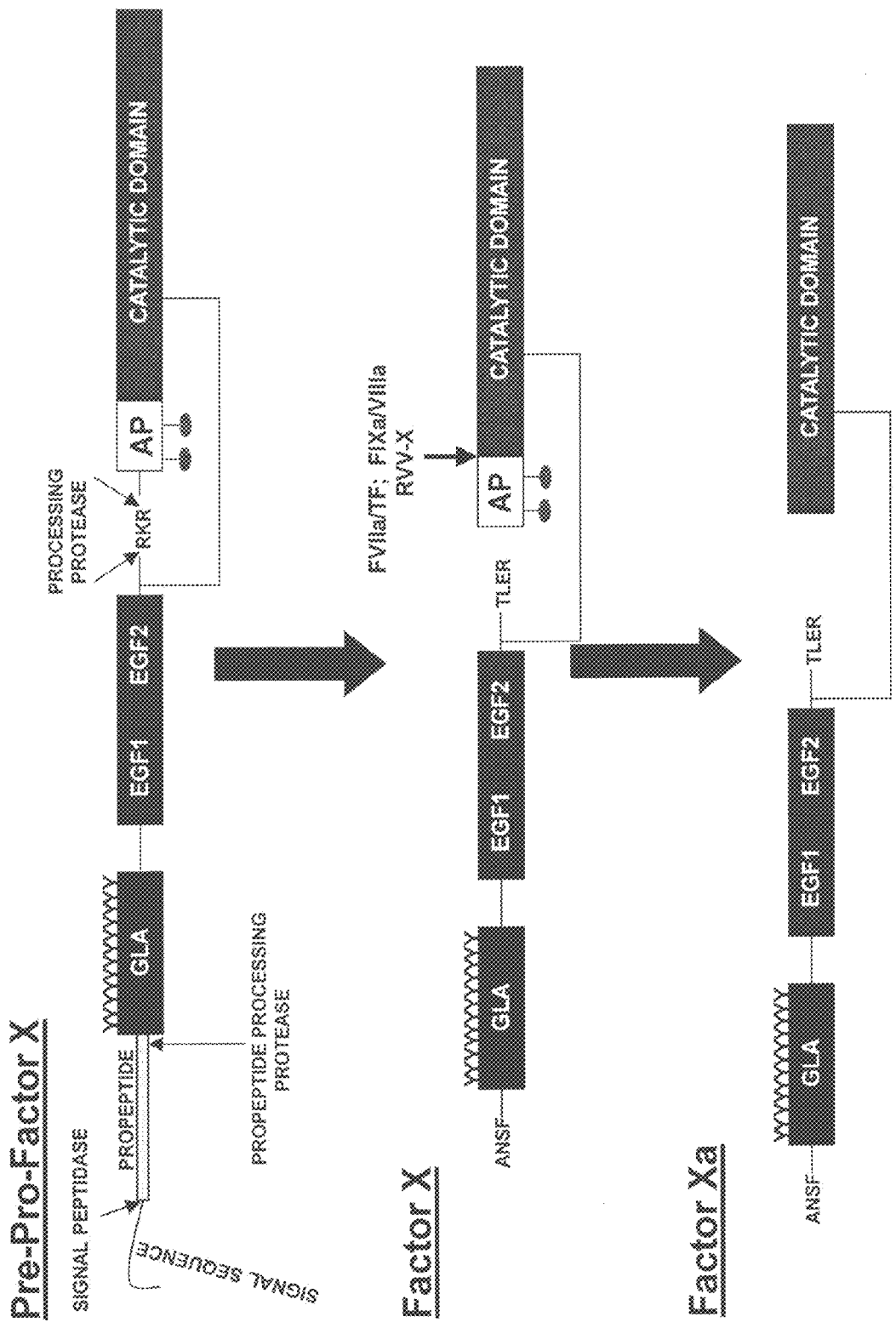
FIG. 1. Processing of Factor X. Factor X is synthesized with a signal sequence and propeptide which are removed prior to its secretion. Factor X is a zymogen and has no enzymatic activity. FX is converted to factor Xa following cleavage at Arg15-Ile16 (positions 234 and 235 in SEQ ID NO: 1) bond releasing an activation peptide (AP). The ANSF sequence is SEQ ID NO: 5 and the TLER sequence is SEQ ID NO: 6.
Figure 2:
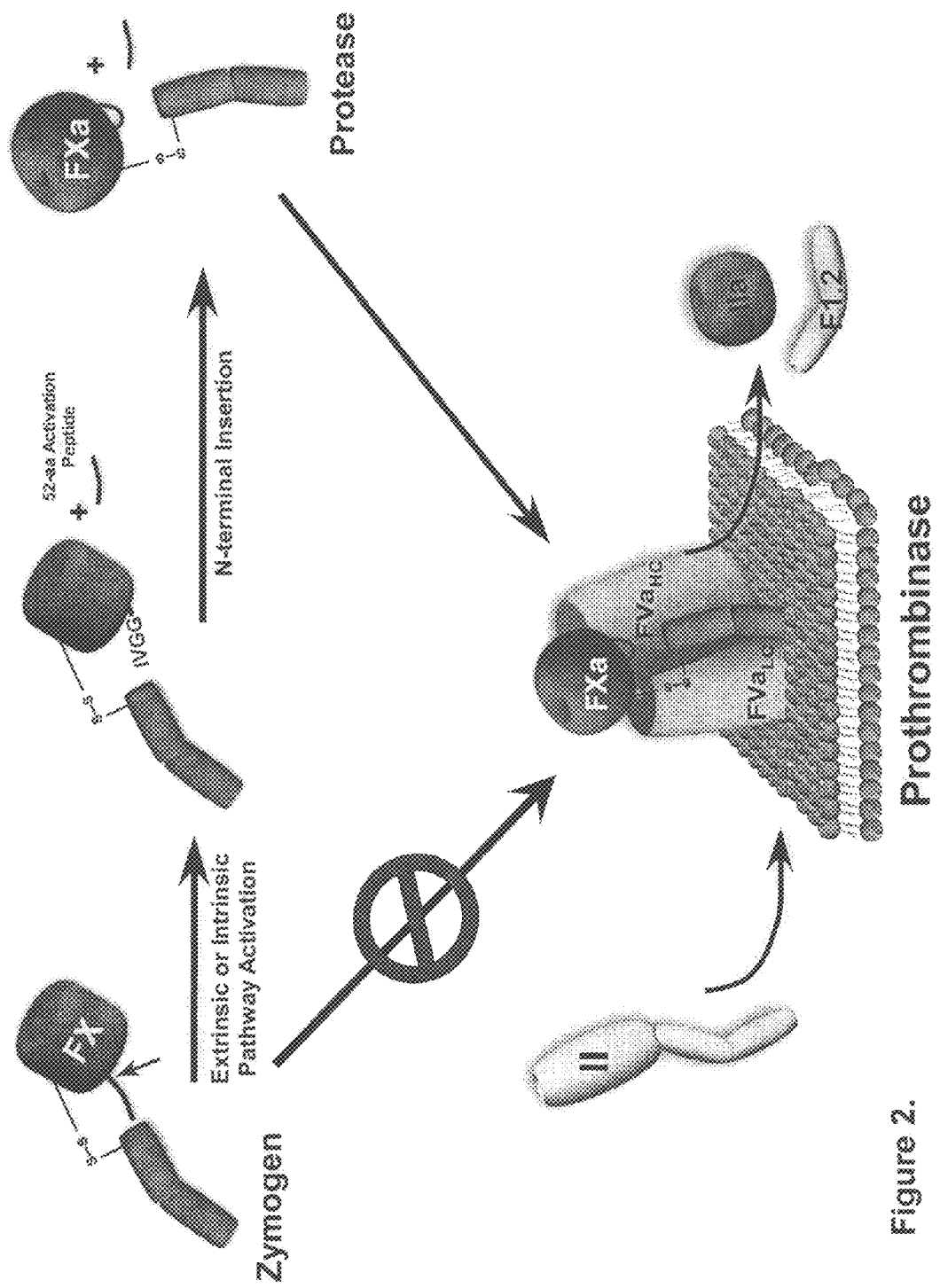
FIG. 2. Zymogen to protease conversion. The zymogen to protease transition for factor X and assembly of factor Xa into prothrombinase (FXa, FVa, phospholipid and calcium ions). This enzyme converts prothrombin (II) to thrombin (IIa). The IVGG sequence is SEQ ID NO: 4.
Figure 3:
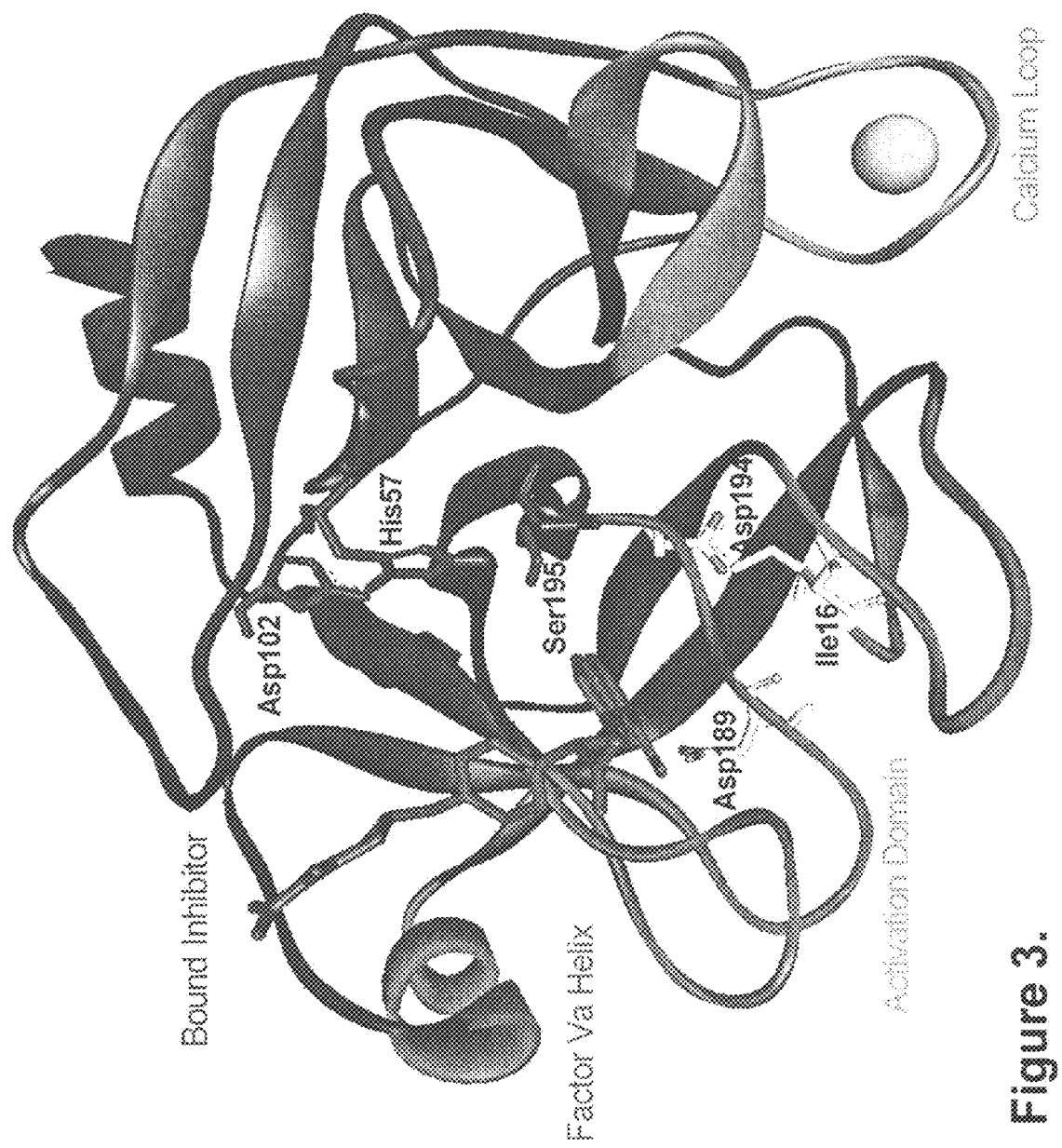
FIG. 3. The X-ray structure of FXa. The catalytic domain of FXa in the standard orientation. Structural regions are noted along with important residues. Taken from Brandstetter et al. (1996) J. Biol. Chem. 271:29988-29992.
Figure 4:
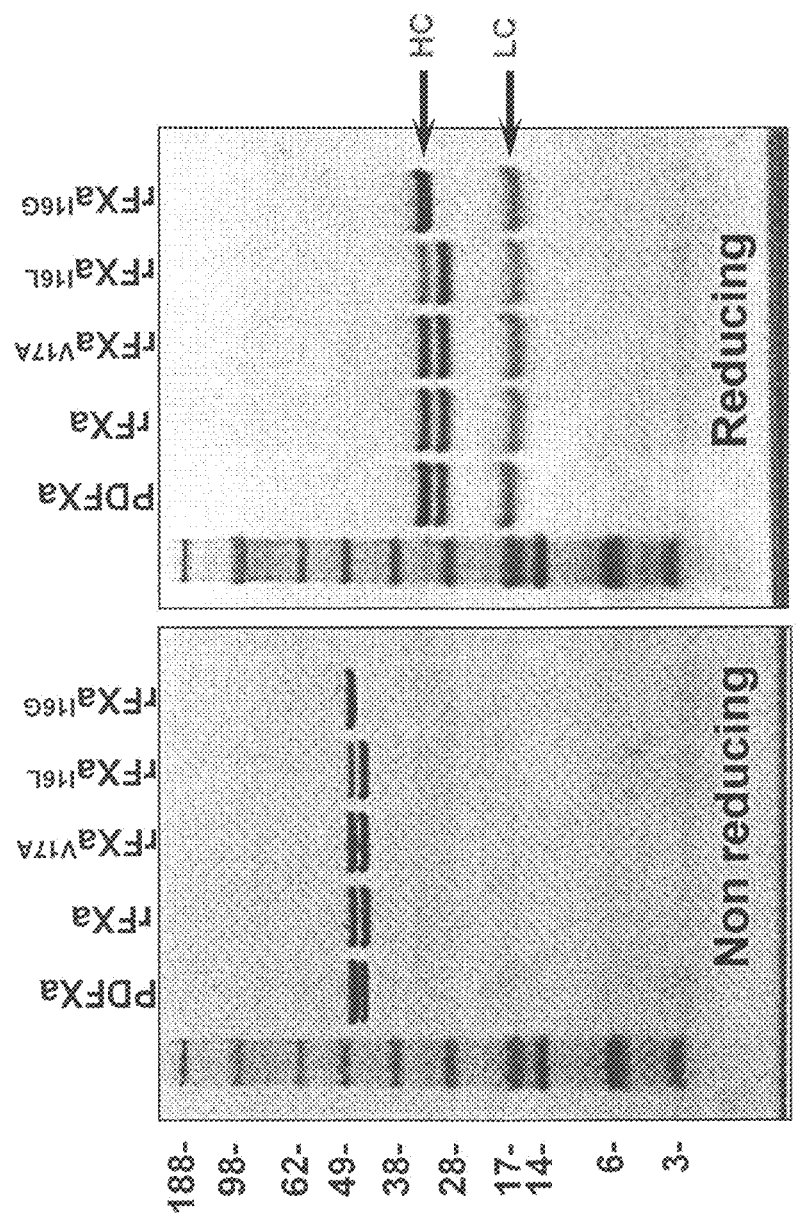
FIG. 4. SDS-PAGE analysis of FX/Xa variants. 4-12% SDS-PAGE gels were run under either non-reducing or reducing conditions and then stained with Coomassie Blue.

Factor X (FX)[1] is a vitamin K-dependent two-chain glycoprotein which plays a central role in blood coagulation (FIG. 1). This serine protease zymogen is a substrate for both the extrinsic (tissue factor/FVIIa) and intrinsic (FVIIIa/FIXa) tenase enzyme complexes which cleave the Arg[15]-Ile[16] (positions 234 and 235 in SEQ ID NO: 1) scissile bond in FX releasing a 52-amino acid activation peptide generating FXa. Factor Xa is the protease responsible for the conversion of prothrombin to thrombin (FIG. 2). Although factor Xa is a fully competent protease and possesses the catalytic machinery for the cleavage of prothrombin, it is a profoundly poor catalyst for this reaction. Its tight binding interaction with the cofactor, factor Va, on a membrane surface profoundly increases the rate of thrombin formation without substantially affecting other reactions catalyzed by factor Xa. Changes to the N-terminal sequence (Ile-Val-Gly) following the Arg15 (position 234 in SEQ ID NO: 1) cleavage site that lead to suboptimal molecular sexuality are expected to yield a "zymogen-like" Xa derivative that has impaired, or even zero, proteolytic activity. These derivatives are not expected to be susceptible to inhibition by plasma protease inhibitors such as Antithrombin III and are not expected to interfere with the initiation of coagulation following vascular damage because they are not expected to bind TFPI very well. Factor Xa binds factor Va tightly while the zymogen factor X does not. Thus, zymogen-like forms of factor Xa are expected to bind Va more weakly but be completely rescued at sufficiently high cofactor concentrations and catalyze thrombin formation efficiently. Zymogen-like forms of factor Xa with these properties are expected to act as long-lived proteases in circulation that are otherwise dead but retain the ability to catalyze thrombin formation upon binding to factor Va. They have the potential to serve as therapeutic procoagulants that bypass deficiencies in other clotting factors in the cascade, without the deleterious effects associated with infusion of fully functional wild type FXa.

I. DEFINITIONS

Various terms relating to the biological molecules of the present invention are used hereinabove and also throughout the specification and claims.

The phrase "variant zymogen/protease" refers to a modified FX zymogen or FXa protease which has been genetically altered such that its protease activity when converted to FXa is reduced or "zymogen-like" in the absence of specific cofactors (e.g., the binding affinity for the active site is lower than that observed in the wild type molecule. Notably, this affinity/activity is restored in the presence of the proper co-factors which include, without limitation factor Va. Preferred sites for amino acid alterations in the parent FX molecule include substitution of the isoleucine at position 235 in SEQ ID NO: 1, substitution of the valine at position 236 in SEQ ID NO: 1, and substitution of the aspartic acid at position 418 in SEQ ID NO: 1, with the proviso that the amino acid at position 235 in SEQ ID NO: 1 is not valine or alanine.

The phrase "hemostasis related disorder" refers to bleeding disorders such as hemophilia A and B, hemophilia A and B patients with inhibitory antibodies, deficiencies in coagulation Factors, VII, IX and X, XI, V, XII, II, von Willebrand factor, combined FV/FVIII deficiency, vitamin K epoxide reductase Cl deficiency, gamma-carboxylase deficiency; bleeding associated with trauma, injury, thrombosis, thrombocytopenia, stroke, coagulopathy, disseminated intravascular coagulation (DIC); over-anticoagulation associated with heparin, low molecular weight heparin, pentasaccharide, warfarin, small molecule antithrombotics (i.e. FXa inhibitors); and platelet disorders such as, Bernard Soulier syndrome, Glanzman thromblastemia, and storage pool deficiency. A hemostasis related disorder can also include bleeding related to thromboic disorders such as deep venous thrombosis, thrombosis associated with cardiovascular disease states or malignancies, thrombosis resulting from in-dwelling catheters or other invasive surgical procedures and thrombosis associated with autoimmune diseases such as lupus. The zymogen/protease variants could also provide necessary hemostasis for patients with disseminated intravascular coagulation or consumptive coagulopathies arising from a variety of disease states.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "promoter region" refers to the transcriptional regulatory regions of a gene, which may be found at the 5' or 3' side of the coding region, or within the coding region, or within introns.

The term "vector" refers to a small carrier DNA molecule into which a DNA sequence can be inserted for introduction into a host cell where it will be replicated. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide sequence or amino acid sequence means a sequence having the properties of a given SEQ ID NO:. For example, when used in reference to an amino acid sequence, the phrase includes the sequence per se and molecular modifications that would not affect the basic and novel characteristics of the sequence.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application for which the oligonucleotide is used.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to act functionally as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product.

The primer may vary in length depending on the particular conditions and requirements of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (found on the world wide web at ncbi.nlm.nih.gov/blast/; Altschul et al., 1990, J Mol Biol 215:403-410) using a gapped alignment with default parameters, may be used to determine the level of identity and similarity between nucleic acid sequences and amino acid sequences.

II. PREPARATION OF VARIANT ZYMOGEN-PROTEASE ENCODING NUCLEIC ACID MOLECULES AND POLYPEPTIDES

A. Nucleic Acid Molecules

Nucleic acid molecules encoding the variant zymogen/proteases of the invention may be prepared by using recombinant DNA technology methods. The availability of nucleotide sequence information enables preparation of isolated nucleic acid molecules of the invention by a variety of means. For example, nucleic acid sequences encoding a zymogen/protease polypeptide may be isolated from appropriate biological sources using standard protocols well known in the art.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell. Alternatively, the nucleic acids may be maintained in vector suitable for expression in mammalian cells. In cases where post-translational modification affects zymogen/protease function (e.g., Factor Xa), it is preferable to express the molecule in mammalian cells.

In one embodiment, the nucleic acids encoding the factor X zymogen variants may be further modified via insertion of an intracellular proteolytic cleavage site. In order to express "activated" zymogen-like FXa variants in mammalian cells, an intracellular proteolytic cleavage site can be inserted between positions Arg15 and 16 (positions 234 and 235 in SEQ ID NO: 1) in the variant FX zymogen. Such cleavage sites include: Arg-Lys-Arg or Arg-Lys-Arg-Arg-Lys-Arg (SEQ ID NO: 3). These cleavage sites are efficiently recognized by proteases (PACE/furin-like enzymes) within the cell and are removed. This results in a processed variant FX(a) in which the heavy chain on the molecule begins now begins at position 235 in SEQ ID NO: 1. Introduction of this cleavage site at said position will allow for the intracellular conversion of FX to FXa.

In another embodiment, the entire 52 amino acid activation peptide can be removed and the intracellular protease cleavage site can be introduced in its place which will result in variant FXa.

Ultimately these types of modifications allow for secretion of the "active" processed form of variant FX from a cell that expresses the modified variant FX. Secretion of the cleaved factor obviates a need for proteolytic cleavage during blood clotting or following the isolation of the protein.

Variant zymogen/protease-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting zymogen/protease expression.

B. Proteins

A full-length or variant zymogen/protease polypeptide of the present invention may be prepared in a variety of ways, according to known methods. The protein may be purified from appropriate sources, e.g., transformed bacterial or animal cultured cells or tissues which express zymogen/protease, by immunoaffinity purification. However, this is not a preferred method due to the low amount of protein likely to be present in a given cell type at any time.

The availability of nucleic acid molecules encoding a variant zymogen/protease polypeptide enables production of zymogen/protease using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of zymogen/protease may be produced by expression in a suitable prokaryotic or eukaryotic expression system. For example, part or all of a DNA molecule encoding variant Factor Xa for example, may be inserted into a plasmid vector adapted for expression in a bacterial cell, such as *E. coli* or a mammalian cell such as CHO or Hela cells. Alternatively, in a preferred embodiment, tagged fusion proteins comprising zymogen/protease can be generated. Such zymogen/protease-tagged fusion proteins are encoded by part or all of a DNA molecule, ligated in the correct codon reading frame to a nucleotide sequence encoding a portion or all of a desired polypeptide tag which is inserted into a plasmid vector adapted for expression in a bacterial cell, such as *E. coli* or a eukaryotic cell, such as, but not limited to, yeast and mammalian cells. Vectors such as those described above comprise the regulatory elements necessary for expression of the DNA in the host cell positioned in such a manner as to permit expression of the DNA in the host cell. Such regulatory elements required for expression include, but are not limited to, promoter sequences, transcription initiation sequences, and enhancer sequences.

Variant zymogen/protease proteins, produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope, GST or the hemagglutinin epitope. Such methods are commonly used by skilled practitioners.

Zymogen/protease proteins, prepared by the aforementioned methods, may be analyzed according to standard procedures. For example, such proteins may be subjected to amino acid sequence analysis, according to known methods.

As discussed above, a convenient way of producing a polypeptide according to the present invention is to express nucleic acid encoding it, by use of the nucleic acid in an expression system. A variety of expression systems of utility for the methods of the present invention are well known to those of skill in the art.

Accordingly, the present invention also encompasses a method of making a polypeptide (as disclosed), the method including expression from nucleic acid encoding the polypeptide (generally nucleic acid). This may conveniently be achieved by culturing a host cell, containing such a vector, under appropriate conditions which cause or allow production of the polypeptide. Polypeptides may also be produced in in vitro systems, such as in reticulocyte lysates.

III. USES OF ZYMOGEN/PROTEASE PROTEINS AND ZYMOGEN/PROTEASE—ENCODING NUCLEIC ACIDS

Variant zymogen/protease nucleic acids encoding polypeptides having altered protease activities may be used according to this invention, for example, as therapeutic and/or prophylactic agents (protein or nucleic acid) which modulate the blood coagulation cascade. The present inventors have discovered that factor X/Xa zymogen/protease molecules can increase coagulation and provide effective hemostasis.

A. Variant Zymogen/Protease Polypeptides

In a preferred embodiment of the present invention, variant zymogen/protease polypeptides may be administered to a patient via infusion in a biologically compatible carrier, preferably via intravenous injection. The variant zymogen/proteases of the invention may optionally be encapsulated into liposomes or mixed with other phospholipids or micelles to increase stability of the molecule. Zymogen/protease may be administered alone or in combination with other agents known to modulate hemostasis (e.g., Factor V, Factor Va or derivatives thereof). An appropriate composition in which to deliver zymogen/protease polypeptides may be determined by a medical practitioner upon consideration of a variety of physiological variables, including, but not limited to, the patient's condition and hemodynamic state. A variety of compositions well suited for different applications and routes of administration are well known in the art and are described hereinbelow.

The preparation containing the purified factor X/Xa analog contains a physiologically acceptable matrix and is preferably formulated as a pharmaceutical preparation. The preparation can be formulated using substantially known prior art methods, it can be mixed with a buffer containing salts, such as NaCl, $CaCl_2$, and amino acids, such as glycine and/or lysine, and in a pH range from 6 to 8. Until needed, the purified preparation containing the factor X/Xa analog can be stored in the form of a finished solution or in lyophilized or deep-frozen form. Preferably the preparation is stored in lyophilized form and is dissolved into a visually clear solution using an appropriate reconstitution solution.

Alternatively, the preparation according to the present invention can also be made available as a liquid preparation or as a liquid that is deep-frozen.

The preparation according to the present invention is especially stable, i.e., it can be allowed to stand in dissolved form for a prolonged time prior to application.

The preparation according to the present invention which contains a factor X analog in combination with factor XIa or a derivative thereof which is able to activate the factor X analog into factor Xa or the factor Xa analog can be made available in the form of a combination preparation comprising a container that holds factor XIa which is immobilized on a matrix, potentially in the form of a miniature column or a syringe complemented with a protease, and a container containing the pharmaceutical preparation with the factor X analog. To activate the factor X analog, the factor X analog-containing solution, for example, can be pressed over the immobilized protease. During storage of the preparation, the factor X analog-containing solution is preferably spatially separated from the protease. The preparation according to the present invention can be stored in the same container as the protease, but the components are spatially separated by an impermeable partition which can be easily removed before administration of the preparation. The solutions can also be stored in separate containers and be brought into contact with each other only shortly prior to administration.

The factor X analog can be activated into factor Xa shortly before immediate use, i.e., prior to the administration to the patient. The activation can be carried out by bringing a factor X analog into contact with an immobilized protease or by mixing solutions containing a protease, on the one hand, and the factor X analog, on the other hand. Thus, it is possible to separately maintain the two components in solution and to mix them by means of a suitable infusion device in which the components come into contact with each other as they pass through the device and thereby to cause an activation into factor Xa or into the factor Xa analog. The patient thus receives a mixture of factor Xa and, in addition, a serine protease which is responsible for the activation. In this context, it is especially important to pay close attention to the dosage since the additional administration of a serine protease also activates endogenous factor X, which may shorten the coagulation time.

The preparation according to the present invention can be made available as a pharmaceutical preparation with factor Xa activity in the form of a one-component preparation or in combination with other factors in the form of a multi-component preparation.

Prior to processing the purified protein into a pharmaceutical preparation, the purified protein is subjected to the conventional quality controls and fashioned into a therapeutic form of presentation. In particular, during the recombinant manufacture, the purified preparation is tested for the absence of cellular nucleic acids as well as nucleic acids that are derived from the expression vector, preferably using a method, such as is described in EP 0 714 987.

Another feature of this invention relates to making available a preparation which contains a factor Xa analog with a high stability and structural integrity and which, in particular, is free from inactive factor X/Xa analog intermediates and autoproteolytic degradation products and which can be produced by activating a factor X analog of the type described above and by formulating it into an appropriate preparation.

The pharmaceutical preparation may contain dosages of between 10-1000 ng/kg, more preferably between about 10-250 ng/kg and most preferably between 10 and 75 ng/kg, with 40 ng/kg of the variant factor X polypeptide being particularly preferred. Patients may be treated immediately upon presentation at the clinic with a bleed. Alternatively, patients may receive a bolus infusion every one to three hours, or if sufficient improvement is observed, a once daily infusion of the variant factor Xa described herein.

B. Zymogen/Protease-Encoding Nucleic Acids

Zymogen/protease-encoding nucleic acids may be used for a variety of purposes in accordance with the present invention. In a preferred embodiment of the invention, a nucleic acid delivery vehicle (i.e., an expression vector) for modulating blood coagulation is provided wherein the expression vector comprises a nucleic acid sequence coding for a variant zymogen/protease polypeptide, or a functional fragment thereof as described herein. Administration of zymogen/protease-encoding expression vectors to a patient results in the expression of zymogen/protease polypeptide which serves to alter the coagulation cascade. In accordance with the present invention, an zymogen/protease encoding nucleic acid sequence may encode an zymogen/protease polypeptide as described herein whose expression increases hemostasis. In a preferred embodiment, a zymogen/protease nucleic acid sequence encodes a human Factor Xa polypeptide variant.

Expression vectors comprising variant X/Xa zymogen/protease nucleic acid sequences may be administered alone, or in combination with other molecules useful for modulating hemostasis. According to the present invention, the expression vectors or combination of therapeutic agents may be administered to the patient alone or in a pharmaceutically acceptable or biologically compatible compositions.

In a preferred embodiment of the invention, the expression vector comprising nucleic acid sequences encoding the variant zymogen/protease variants is a viral vector. Viral vectors which may be used in the present invention include, but are not limited to, adenoviral vectors (with or without tissue specific promoters/enhancers), adeno-associated virus (AAV) vectors of multiple serotypes (e.g., AAV-2, AAV-5, AAV-7, and AAV-8) and hybrid AAV vectors, lentivirus vectors and pseudo-typed lentivirus vectors [e.g., Ebola virus, vesicular stomatitis virus (VSV), and feline immunodeficiency virus (FIV)], herpes simplex virus vectors, vaccinia virus vectors, and retroviral vectors.

In a preferred embodiment of the present invention, methods are provided for the administration of a viral vector comprising nucleic acid sequences encoding a variant zymogen/protease, or a functional fragment thereof. Adenoviral vectors of utility in the methods of the present invention preferably include at least the essential parts of adenoviral vector DNA. As described herein, expression of a variant zymogen/protease polypeptide following administration of such an adenoviral vector serves to modulate hemostasis. In the context of the variant Factor Xa described herein, such administration enhances the procoagulation activity of the protease.

Recombinant adenoviral vectors have found broad utility for a variety of gene therapy applications. Their utility for such applications is due largely to the high efficiency of in vivo gene transfer achieved in a variety of organ contexts.

Adenoviral particles may be used to advantage as vehicles for adequate gene delivery. Such virions possess a number of desirable features for such applications, including: structural features related to being a double stranded DNA nonenveloped virus and biological features such as a tropism for the human respiratory system and gastrointestinal tract. Moreover, adenoviruses are known to infect a wide variety of cell types in vivo and in vitro by receptor-mediated endocytosis. Attesting to the overall safety of adenoviral vectors, infection with adenovirus leads to a minimal disease state in humans comprising mild flu-like symptoms.

Due to their large size (~36 kilobases), adenoviral genomes are well suited for use as gene therapy vehicles because they can accommodate the insertion of foreign DNA following the removal of adenoviral genes essential for replication and nonessential regions. Such substitutions render the viral vector impaired with regard to replicative functions and infectivity. Of note, adenoviruses have been used as vectors for gene therapy and for expression of heterologous genes.

For a more detailed discussion of the use of adenovirus vectors utilized for gene therapy, see Berkner, 1988, Biotechniques 6:616-629 and Trapnell, 1993, Advanced Drug Delivery Reviews 12:185-199.

It is desirable to introduce a vector that can provide, for example, multiple copies of a desired gene and hence greater amounts of the product of that gene. Improved adenoviral vectors and methods for producing these vectors have been described in detail in a number of references, patents, and patent applications, including: Mitani and Kubo (2002, Curr Gene Ther. 2(2):135-44); Olmsted-Davis et al. (2002, Hum Gene Ther. 13(11):1337-47); Reynolds et al. (2001, Nat. Biotechnol. 19(9):838-42); U.S. Pat. No. 5,998,205 (wherein tumor-specific replicating vectors comprising multiple DNA copies are provided); U.S. Pat. No. 6,228,646 (wherein helper-free, totally defective adenovirus vectors are described); U.S. Pat. No. 6,093,699 (wherein vectors and methods for gene therapy are provided); U.S. Pat. No. 6,100, 242 (wherein a transgene-inserted replication defective adenovirus vector was used effectively in in vivo gene therapy of peripheral vascular disease and heart disease); and International Patent Application Nos. WO 94/17810 and WO 94/23744.

For some applications, an expression construct may further comprise regulatory elements which serve to drive expression in a particular cell or tissue type. Such regulatory elements are known to those of skill in the art and discussed in depth in Sambrook et al. (1989) and Ausubel et al. (1992). The incorporation of tissue specific regulatory elements in the expression constructs of the present invention provides for at least partial tissue tropism for the expression of the variant zymogen/proteases or functional fragments thereof. For example, an E1 deleted type 5 adenoviral vector comprising nucleic acid sequences encoding variant zymogen/protease under the control of a cytomegalovirus (CMV) promoter may be used to advantage in the methods of the present invention.

Exemplary Methods for Producing Adenoviral Vectors

Adenoviral vectors for recombinant gene expression have been produced in the human embryonic kidney cell line 293 (Graham et al., 1977, J. Gen. Virol. 36:59-72). This cell line is permissive for growth of adenovirus 2 (Ad2) and adenovirus 5 mutants defective in E1 functions because it comprises the left end of the adenovirus 5 genome and, therefore, expresses E1 proteins. E1 genes integrated into the cellular genome of 293 cells are expressed at levels which facilitate the use of these cells as an expression system in which to amplify viral vectors from which these genes have been deleted. 293 cells have been used extensively for the isolation and propagation of E1 mutants, for helper-independent cloning, and for expression of adenovirus vectors. Expression systems such as the 293 cell line, therefore, provide essential viral functions in trans and thereby enable propagation of viral vectors in which exogenous nucleic acid sequences have been substituted for E1 genes. See Young et al. in The Adenoviruses, Ginsberg, ed., Plenum Press, New York and London (1984), pp. 125-172.

Other expression systems well suited to the propagation of adenoviral vectors are known to those of skill in the art (e.g., HeLa cells) and have been reviewed elsewhere.

Also included in the present invention is a method for modulating hemostasis comprising providing cells of an individual with a nucleic acid delivery vehicle encoding a variant zymogen/protease polypeptide and allowing the cells to grow under conditions wherein the zymogen/protease polypeptide is expressed.

From the foregoing discussion, it can be seen that zymogen/protease polypeptides, and zymogen/protease polypeptide expressing nucleic acid vectors may be used in the treatment of disorders associated with aberrant blood coagulation.

C. Pharmaceutical Compositions

The expression vectors of the present invention may be incorporated into pharmaceutical compositions that may be delivered to a subject, so as to allow production of a biologically active protein (e.g., a variant zymogen/protease polypeptide or functional fragment or derivative thereof). In a particular embodiment of the present invention, pharmaceutical compositions comprising sufficient genetic material to enable a recipient to produce a therapeutically effective amount of a variant zymogen/protease polypeptide can influence hemostasis in the subject. Alternatively, as discussed above, an effective amount of the variant Factor X polypeptide may be directly infused into a patient in need thereof. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents (e.g., co-factors) which influence hemostasis.

In preferred embodiments, the pharmaceutical compositions also contain a pharmaceutically acceptable excipient. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., 18th Edition, Easton, Pa. [1990]).

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they may be placed in an appropriate container and labeled for treatment. For administration of zymogen/protease-containing vectors or polypeptides, such labeling would include amount, frequency, and method of administration.

Pharmaceutical compositions suitable for use in the invention include compositions wherein the active ingredients are contained in an effective amount to achieve the intended therapeutic purpose. Determining a therapeutically effective dose is well within the capability of a skilled medical practitioner using the techniques and guidance provided in the present invention. Therapeutic doses will depend on, among other factors, the age and general condition of the subject, the severity of the aberrant blood coagulation phenotype, and the strength of the control sequences regulating the expression levels of the variant zymogen/protease polypeptide. Thus, a therapeutically effective amount in humans will fall in a relatively broad range that may be determined by a medical practitioner based on the response of an individual patient to vector-based zymogen/protease treatment.

D. Administration

The variant Factor X polypeptides, alone or in combination with other agents may be directly infused into a patient in an appropriate biological carrier as described hereinabove. Expression vectors of the present invention comprising nucleic acid sequences encoding variant zymogen/protease, or functional fragments thereof, may be administered to a patient by a variety of means (see below) to achieve and maintain a prophylactically and/or therapeutically effective level of the zymogen/protease polypeptide. One of skill in the art could readily determine specific protocols for using the zymogen/protease encoding expression vectors of the present invention for the therapeutic treatment of a particular patient. Protocols for the generation of adenoviral vectors and administration to patients have been described in U.S. Pat. Nos. 5,998,205; 6,228,646; 6,093,699; 6,100,242; and International Patent Application Nos. WO 94/17810 and WO 94/23744, which are incorporated herein by reference in their entirety.

Variant zymogen/protease encoding adenoviral vectors of the present invention may be administered to a patient by any means known. Direct delivery of the pharmaceutical compositions in vivo may generally be accomplished via injection using a conventional syringe, although other delivery methods such as convection-enhanced delivery are envisioned (See e.g., U.S. Pat. No. 5,720,720). In this regard, the compositions may be delivered subcutaneously, epidermally, intradermally, intrathecally, intraorbitally, intramucosally, intraperitoneally, intravenously, intraarterially, orally, intrahepatically or intramuscularly. Other modes of administration include oral and pulmonary administration, suppositories, and transdermal applications. A clinician specializing in the treatment of patients with blood coagulation disorders may determine the optimal route for administration of the adenoviral vectors comprising zymogen/protease nucleic acid sequences based on a number of criteria, including, but not limited to: the condition of the patient and the purpose of the treatment (e.g., enhanced or reduced blood coagulation).

The present invention also encompasses AAV vectors comprising a nucleic acid sequence encoding a variant zymogen/protease polypeptide.

Also provided are lentivirus or pseudo-typed lentivirus vectors comprising a nucleic acid sequence encoding a variant zymogen/protease polypeptide Also encompassed are naked plasmid or expression vectors comprising a nucleic acid sequence encoding a variant zymogen/protease polypeptide.

Example 1

Variant Factor Xa Zymogen/Protease

Proteolytic processing of precursor plasma proteins to affect activation is a hallmark of blood coagulation. The paradigm for this type of activation mechanism is the zymogen to protease transition in the chymotrypsin-like serine protease family. Bond cleavage at a highly conserved site (Arg15-Ile16 chymotrypsin numbering system; i.e., at positions 234 and 235 of SEQ ID NO: 1) unmasks a new N-terminus which acts as an intramolecular ligand for Asp194 (position 418 in SEQ ID NO: 1) (FIG. 2). This new salt-bridge results in or is associated with a conformational change and ordering of the so-called "activation domain", surface loops consisting of the S1 specificity pocket, oxyanion hole, autolysis loop, and sodium biding site (FIG. 3). It is well documented in the trypsin system that Ile16-Asp194 (positions 235 and 418 in SEQ ID NO: 1) internal salt-bridge formation is allosterically linked to the S1 specificity site; that is changes at one site influence the other site and vice versa.

The basic principles of the zymogen to active enzyme transition for serine proteases at the structural level are well documented, particularly for chymotrypsin and trypsin and these examples serve as the paradigm for the serine protease family. General aspects can be summarized as follows (see FIG. 2): 1) the structure (~80-85%) of the zymogen is relatively similar to the protease; 2) the transition is initiated following liberation of a highly conserved N-terminus (for example, Ile16-Val-Gly-Gly19 (SEQ ID NO: 4) corresponding to positions 235-238 of SEQ ID NO: 1); 3) the new free α-amino group (Ile16; position 235 in SEQ ID NO: 1) becomes buried in a hydrophobic environment and its α-amino nitrogen forms an internal salt bridge with Asp194 (position 418 in SEQ ID NO: 1); 4) the position of Asp194 (position 418 in SEQ ID NO: 1) changes significantly upon zymogen activation rotating ~170°; and 5) this internal salt bridge results in or is associated with a conformational change in the so-called "activation domain", surface exposed loops consisting of residues 16-19, 142-153, 184-194, and 216-223; and partially comprising the S1 specificity site (nomenclature of Schechter and Berger (1967) Bochem. Biophys. Res. Comm. 43:694-702) and oxyanion hole. Various studies indicate that the zymogen and the mature enzyme exist in an equilibrium, with Keq=~$10^8$ in favor of the zymogen. Bode and colleagues have elegantly demonstrated that trypsinogen can adopt an active trypsin-like structure upon strong ligand binding to the S1 specificity pocket or suitable ligands with high affinity for the Ile16 (position 235 in SEQ ID NO: 1) cleft. Additional examples of this induction without cleavage of the Arg/Lys15-Ile16 (positions 234 and 235 in SEQ ID NO: 1) bond include the binding of streptokinase to plasminogen, staphylocoagulase to prothrombin, and a recently described autoantibody to prothrombin (Madoiwa et al. (2001) Blood 97:3783-3789). Collectively these studies indicate that serine proteases, even in their zymogen forms, can adopt protease-like functions depending upon various environmental conditions, i.e. strong ligand binding to the zymogen.

It is well known that the activation of FX results in major conformational changes in the serine protease domain which are accompanied by the ability of the protease to bind with much greater affinity to S1-directed probes and membrane-bound FVa (1-6). The overall molecular mechanism(s) which governs the transition of serine proteases is generally assumed to follow that of the trypsin system. However, this may not uniformly be the case. Single-chain tPA employs a different molecular strategy to maintain its zymogen-like state (8-11). Analysis of zymogen/protease pairs involved in blood coagulation, particularly FVII/FVIIa, indicates that several differences exist in this transition compared to the trypsin system (12). While several structural determinants on FXa are part of the so-called activation domain, it is currently unclear if formation of these sites is directly linked to the zymogen to protease transition. A recently described model of the zymogen FX suggests however that several of these elements may be disordered in the zymogen (13). Comparison of the zymogen model with the active enzyme reveals that residues making up the $Ca^{2+}$ (Asp70-Glu80), $Na^+$ (Ala183-Asp194; Gly219-Gly226) and autolysis loops (Thr144-Arg150) undergo major changes in their backbone positions upon the zymogen to protease transition. Since it is already well-documented, at least for trypsinogen/trypsin, that the S1 specificity site and formation of Ile16-Asp194 (positions 235 and 418 in SEQ ID NO: 1) are allosterically linked, it is reasonable to hypothesize that other elements of the activation domain are also linked to the zymogen to protease transition. In the present example, we have designed experiments to test the hypothesis that destabilization of the Ile16-Asp194 (positions 235 and 418 in SEQ ID NO: 1) internal salt bridge by making changes to position 16, 17, or 194 (positions 235, 236, and 418 in SEQ ID NO: 1) alters the active site cleft making the resulting variant "zymogen-like". We also hypothesized that these changes would allosterically modulate FVa binding.

Materials and Methods

Expression of Factor Xa

While there are several reports in the literature on the expression of rFX, most have relied on truncated versions or have not provided adequate characterization (15-20). Our initial attempts at expressing rFX in HEK 293 cells resulted in expression levels in the range of 1-2 mg rFX/L of conditioned media; however, only 10-40% of the material produced was found to be fully γ-carboxylated (21). The remaining material showed no γ-carboxylation. We took advantage of the different binding affinities of the vitamin K-dependent propeptides for the carboxylase and hypothesized that since the prothrombin propeptide exhibits the lowest affinity for the carboxylase, exchanging the propeptide of FX (highest affinity) with that of prothrombin may enhance γ-carboxylation by allowing for greater substrate turnover (22, 23). Using this new vector, stable transfectants of HEK 293 cells were selected, expanded, and rFX was purified by immunoaffinity chromatography. Phosphate elution from hydroxyapatite was used to separate carboxylated material away from uncarboxylated material. Our results, obtained now from over 30 stable cell lines indicate that on average ~80-90% of the rFX is fully γ-carboxylated compared to 10-40% using the native FX propeptide. These results have recently been published and this strategy has subsequently been employed by at least one other laboratory (24,25). Thus, using this new expression system we are now producing milligram quantities (15-25 mg of fully γ-carboxylated rFX from ~10 L of conditioned media) of protein for detailed structure/function studies.

Enzyme Assays

Enzyme concentrations will be determined by active-site titration with ρ-nitrophenyl ρ-guanidinobenzoate (IIa) or fluorescein mono-ρ-guanidinobenzoate (FXa) (26, 27). FXa chromogenic substrate activity, in the presence or absence of various inhibitors, will be measured from initial rates of hydrolysis of Spectrozyme FXa, S-2222, or S-2765 as previously described (14). Kinetic parameters will be determined by least-squares fitting of the initial rate data to appropriate equations.

Generation of FXa Variants

The FX mutants were generated using the Quick-change site-directed mutagenesis kit (Stratagene) and the entire FX cDNA was sequenced to verify the identity of the product. The various plasmids were transiently transfected into HEK 293 cells using Lipofectamine-2000. 48 hr post-transfection, media was collected and FX antigen levels were determine using a FX-specific ELISA and FXa activity was assessed by chromogenic assay prior to activation by RVV-X or by tissue factor-FVIIa.

Results

Generation of FXa species distributed along the zymogen-protease transition pathway is outlined in Table 1. Transient transfection results indicate that we have generated a series of FXa variants with variable amounts of activity, ranging from ~25% to <1%. We hypothesize that these differences in activity likely reflect FX variants which are shifted to varying degrees along the zymogen to protease transition. Stated differently, the Ile16-Asp194 (positions 235 and 418 in SEQ ID NO: 1) internal salt bridge is stabilized to varying degrees depending upon the amino acid at positions 16, 17 or 194 (positions 235, 236, and 418 in SEQ ID NO: 1). We have chosen three of these variants (rFXaI16L (FXaI235L according to position in SEQ ID NO: 1), FXaI16G (FXaI235G according to position in SEQ ID NO: 1) and FXaV17A (FXaV236A according to position in SEQ ID NO: 1)) for further characterization.

TABLE 1

Activation of Various rFX Variants with RVV-X and TF-FVIIa

| | | | Activation of FX with RVV-X: | | Activation of FX with TF-FVIIa: | |
|---|---|---|---|---|---|---|
| Constructs | [a][FX] (nM) | % wt-Antigen | [b]FXa Activity (nM) | [c]% wt | [b]FXa Activity (nM) | [c]% wt |
| rwt-FX | 54.07 | 100.00 | 10.95 | 100.00 | 18.905 | 100.00 |
| Ile16→Leu | 24.88 | 46.03 | 0.25 | 5.00 | 0.572 | 6.57 |
| Ile16→Phe | 49.48 | 91.51 | 0.01 | 0.08 | 0.004 | 0.02 |
| Ile16→Asp | 12.04 | 22.27 | 0.01 | 0.22 | 0.000 | 0.00 |
| Ile16→Qy | 27.88 | 51.56 | 0.00 | 0.05 | 0.037 | 0.38 |
| Val17→Leu | 28.18 | 52.12 | 1.22 | 21.33 | 3.003 | 30.48 |
| Val17→Ala | 55.88 | 103.36 | 0.34 | 3.02 | 1.029 | 5.27 |
| Val17→Gly | 47.76 | 88.34 | 0.02 | 0.21 | 0.036 | 0.22 |
| Asp194→Asn | 17.32 | 32.04 | 0.03 | 0.79 | 0.000 | 0.00 |
| Asp194→Qu | 30.97 | 57.29 | 0.02 | 0.27 | 0.000 | 0.00 |

[a]Antigen levels are calculated from a FX-specific ELISA and expressed as nM FX

[b]FXa activity levels are based on the rate of peptidyl substrate hydrolysis following activation by RVV-X or TF-FVIIa of a given FX variant and initial rates of hydrolysis are compared to FXa standard curve.

[c]% wt values are based upon comparison to wt-FXa activity levels. The values have been adjusted for antigen levels.

Ile16 = amino acid 235 in SEQ ID NO: 1; Val17 = amino acid 236 in SEQ ID NO: 1; Asp194 = amino acid 418 in SEQ ID NO: 1.

Stable cell lines in HEK293 cells were established and each of the zymogens were purified from 10 L of conditioned media (14, 24). The variants were activated with RVV-X and subsequently purified by gel filtration chromatography (14, 24). SDS-PAGE of the variants prior to and following activation (reducing and non-reducing) is shown in FIG. 4.

We first focused on assessing changes to the active site environment of each of the variants using specific probes that target this region of FXa. Kinetic studies using peptidyl substrates and active site directed probes revealed that FXaI16L (FXaI235L) and FXaV17A (FXaV236A) have an impaired ability to bind these probes (15 to 25-fold increase in the Km or Ki) while the rate of catalysis (kcat) was reduced by 3-fold compared to wild-type FXa (plasma-derived and recombinant) (Tables 2 and 3). Factor Xa 116G (1235G) was not inhibited by any of the probes examined and its chromogenic activity was severely impaired (500 to 1000-fold) precluding calculation of kinetic parameters. These data are consistent with the idea that destabilization of internal salt-bridge formation (Ile16-Asp194; positions 235 and 418 of SEQ ID NO: 1), influences binding at the S1 specificity site. In contrast to these results, the assembly of FXaI16L (FXaI235L) and FXaV17A (FXaV236A) into prothrombinase almost completely restored the Km for peptidyl substrates while the kcat was still 3-fold reduced, indicating that FVa binding can rescue binding at the active site (Tables 2 and 3). Surprisingly even the Km value for 116G (1235G) was almost completely restored (3-fold increased compared to wild-type FXa) when assembled in prothrombinase; however a 60-fold reduction in the kcat was found.

TABLE 2

| Kinetic constants for chromogenic substrate cleavage | | | | |
|---|---|---|---|---|
| Enzyme Species | | $K_m$ (μM) ± SD | | $k_{cat}$ ($sec^{-1}$) ± SD |
| | | Factor Xa | | |
| rwtFXa | | 88.8 ± 11.4 | | 215 ± 13.5 |
| $rFXa^{V17A}$ | 15X | 1377 ± 332 | 3X | 71.6 ± 13.5 |
| $rFXa^{I16L}$ | | 1149 ± 244 | | 57.3 ± 3.1 |
| $rFXa^{I16G}$ | | 1608 ± 423 | | 0.28 ± 0.05 |
| | | Prothrombinase | | |
| rwtFXa | | 130 ± 11 | | 141 ± 3.7 |
| $rFXa^{V17A}$ | 3X | 362 ± 42 | 3X | 68.2 ± 9.7 |
| $rFXa^{I16L}$ | | 296 ± 54 | | 32.5 ± 3.1 |
| $rFXa^{I16G}$ | | 433 ± 31 | 60X | 1.92 ± 0.05 |

For experiments in which free factor Xa was used, 2.0 nM wild-type or 6.0 nM mutant factor Xa was incubated with increasing concentrations of Spectrozyme FXa and for experiments in which prothrombinase was employed 5.0 nM wild-type or mutant factor Xa was incubated with 30 nM factor Va, 50 μM PCPS and increasing concentrations of substrate (10 to 500 μM). hromogenic activity was assessed by monitoring the increase in absorbance at 405 nm over time. The errors in the fitted constants represent 95% confidence limits. Ile16 = amino acid 235 in SEQ ID NO: 1 and Val17 = amino acid 236 in SEQ ID NO: 1.

Consistent with these data, kinetic studies using prothrombin revealed that the Km values obtained for each of these variants assembled in prothrombinase were essentially equivalent to the wild-type enzyme, while the kcat values where reduced to a similar extent as for the chromogenic substrates (Table 4). Taken together, our results indicate that the zymogen to protease transition for FX not only influences the formation of the S1 site, but also contributes in a substantial way to the formation of a FVa binding site. Since direct binding of these FXa variants to FVa rescues binding at S1 site, allosteric linkage likely exists between these sites. Collectively these studies have illustrated a unique way to modify the zymogen to protease transition pathway and have revealed a possible way to develop zymogen-like forms of enzymes which are "activated" following strong ligand binding such as cofactor proteins.

TABLE 4

| Kinetic constants for prothrombin cleavage | | | | |
|---|---|---|---|---|
| Enzyme species | $K_m$ ± SD (μM) | $V_{max}/E_t$ ± SD (nM IIa/min/nM E) | | $V_{max}/E_t \cdot K_m$ ($\mu M^{-1} \cdot s^{-1}$) |
| pdFXa | 0.42 ± 0.02 | 2424 ± 54 | | 96 |
| rFXa | 0.35 ± 0.01 | 1937 ± 26 | 3X | 92 |
| $FXa^{V17A}$ | 0.47 ± 0.03 | 887 ± 26 | | 31 |
| $FXa^{I16L}$ | 0.31 ± 0.02 | 619 ± 14 | | 33 |

Ile16 = amino acid 235 in SEQ ID NO: 1 and Val17 = amino acid 236 in SEQ ID NO: 1.

The results obtained with the chromogenic substrate and the active site-directed inhibitors, indicate that the zymogen-like FXa variants bind to active site probes with reduced affinity. However, assembly of these variants into prothrombinase significantly improves the affinity for active site probes, suggesting that FVa binding can rescue binding at the active site. We next investigated whether the reverse is also true, that is occupation of the zymogen-like active site influences binding to FVa. In order to assess this hypothesis we measured the binding constants between FVa and FXaI16L (FXaI235L) and FXaV17A (FXaV236A). To accomplish this we incubated FVa with a fluorescent derivative of inactive wtFXa in the presence of synthetic phospholipid vesicles and Ca2+ ions. The formation of the complex results in the increase of the fluorescent signal relative to fluorescent FXa alone. We then added increasing concentrations of a non-fluorescent FXa which, if it can bind FVa, will displace the fluorescent FXa, resulting in a decrease of the fluorescent signal. As a control we added S195A FXa as a competitor. This mutant is inactive because it is missing the Ser of the catalytic triad, but has a high affinity for FVa (Table 5). In contrast, when we added either FXaI16L (FXaI235L) or FXaV17A (FXaV236A) the affinity of these zymogen-like variants for FXa was significantly reduced compared to FXaS195A (Table 5). We next examined whether covalent occupation of the active site of FXaI16L (FXaI235L) could restore binding to FVa. To do this we modified the active site of wild-type FXa and FXaI16L (FXaI235L) with an irreversible inhibitor (EGR-chloromethyl ketone) and then repeated the experiment. The data show that that active site blocked FXaI16L (FXaI235L) bound FVa-membranes with the same affinity as wild-type active site blocked FXa. This indicates that occupation of the zymogen-like FXa active site has a direct influence on the binding to FVa.

TABLE 3

| Kinetic constants for inhibition of FXa and prothrombinase | | | | | | |
|---|---|---|---|---|---|---|
| | | $K_i$ (μM) ± SD | | | | |
| Enzyme Species Factor Xa | | Pefabloc tPa/Xa | | Para-amino benzamidine | | $k_2$ ($M^{-1} s^{-1}$) ± SD × $10^3$ Antithrombin III |
| rwtFXa | | 0.070 ± 0.002 | | 78.1 ± 1.5 | | 1.37 ± 0.02 |
| $rFXa^{V17A}$ | 25X | 1.695 ± 0.072 | 11X | 996 ± 37 | 19X | 0.09 ± 0.003 |
| $rFXa^{I16L}$ | | 1.701 ± 0.065 | | 726 ± 40 | | 0.06 ± 0.001 |
| | | | | Prothrombinase | | |
| rwtFXa | | 0.050 ± 0.002 | | 48.6 ± 0.6 | | 0.28 ± 0.01 |
| $rFXa^{V17A}$ | 5X | 0.295 ± 0.013 | 3X | 191 ± 6.4 | 4X | 0.05 ± 0.001 |
| $rFXa^{I16L}$ | | 0.209 ± 0.005 | | 143 ± 9.0 | | 0.09 ± 0.003 |

Ile16 = amino acid 235 in SEQ ID NO: 1 and Val17 = amino acid 236 in SEQ ID NO: 1.

TABLE 5

Equilibrium binding constants for prothrombinase assembly

| Enzyme species | $K_d \pm SD$ (nM) |
|---|---|
| rFXa$^{S195A}$ | 1.34 ± 0.17 |
| rFXa$^{V17A}$ | 7.25 ± 0.65 |
| rFXa$^{I16L}$ | 13.81 ± 1.07 |
| EGR-FXa | 1.80 ± 0.42 |
| EGR-FXa$^{I16L}$ | 1.92 ± 0.20 |

Ile16 = amino acid 235 in SEQ ID NO: 1 and Val17 = amino acid 236 in SEQ ID NO: 1.

Figure 6:
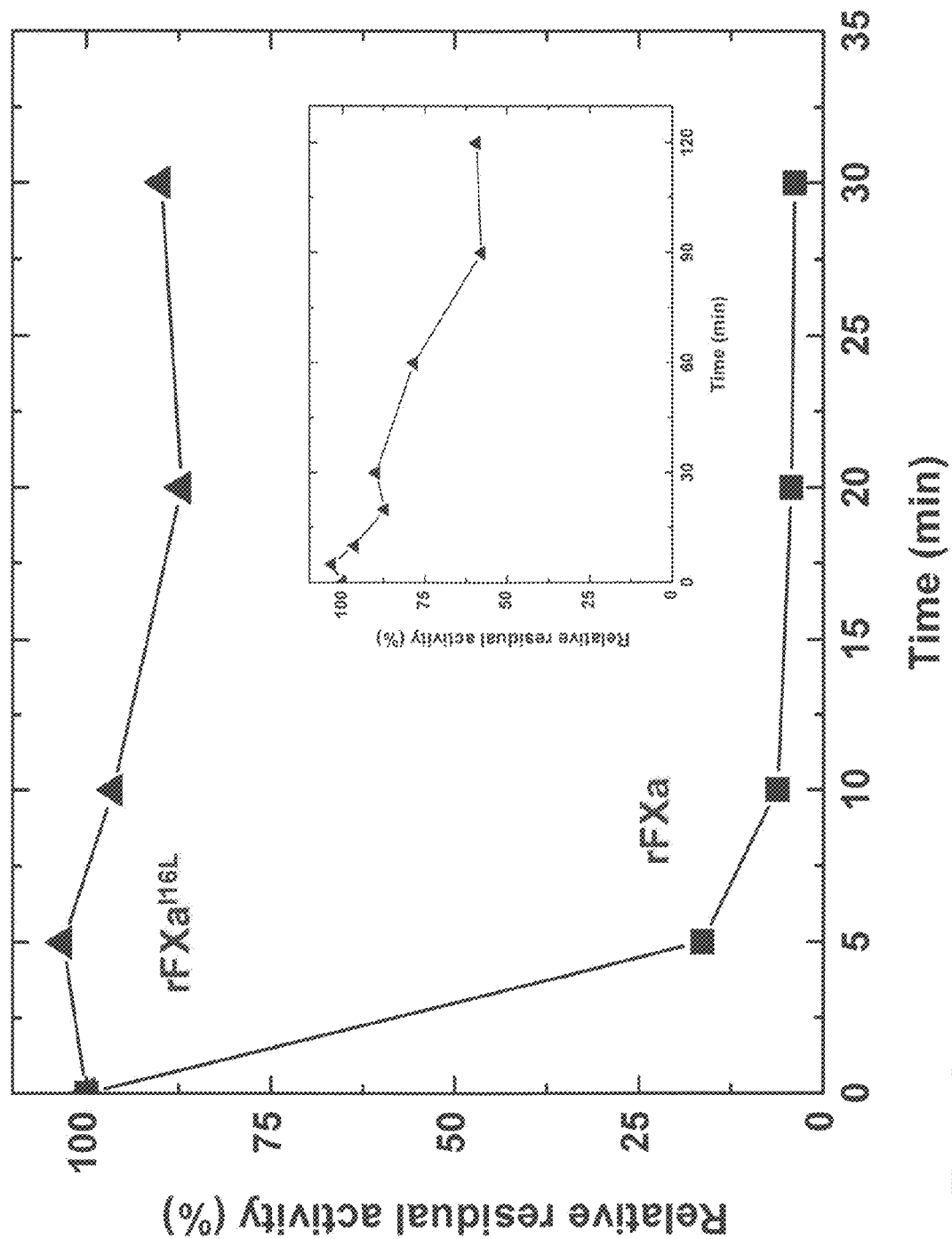
FIG. 6. Factor Xa activity in hemophilia B plasma. Wild-type FXa or FXaI16L (2 nM) were added to hemophilia B plasma and at select time intervals the samples were diluted (0.1 nM) and assayed in an aPTT clotting assay.

Based on the observation that the zymogen-like FXa derivatives have poor reactivity with active-site directed probes and inhibitors in the absence of FVa, but apparently near normal activity when the variants are assembled in prothrombinase, we next evaluated the activity of FXaI16L (FXaI235L) in a plasma environment. Hemophilic A (data not shown) or B plasma was spiked with wild-type FXa to correct the clotting time (aPTT) of these plasmas; 0.1 nM wtFXa gave a clotting time of ~32 sec. The addition of the same concentration of FXaI16L (FXaI235L) gave a clot time of ~42 sec which is ~50-70% of the activity relative to wtFXa, suggesting that this zymogen-like variant has almost normal clotting activity in plasma. Next we monitored the half-life of wild-type FXa and FXaI16L (FXaI235L) in hemophilia B plasma. The proteins were added to HB plasma and at different time points, an aliquot of the mixture was withdrawn and assayed in an aPTT-based assay. The results with HB plasma show that the relative residual activity of wild-type FXa was inhibited very rapidly (<2-min) (FIG. 6). In contrast, the activity of FXaI16L (FXaI235L) persisted for a much longer time with an estimated half-life of >2 hours. Similar results were found with hemophilia A plasma. These results suggest that it is possible to modulate the characteristics of an enzyme so that it has a long half-life in plasma and can correct the clotting time of a hemophilic plasma.

Figure 7:
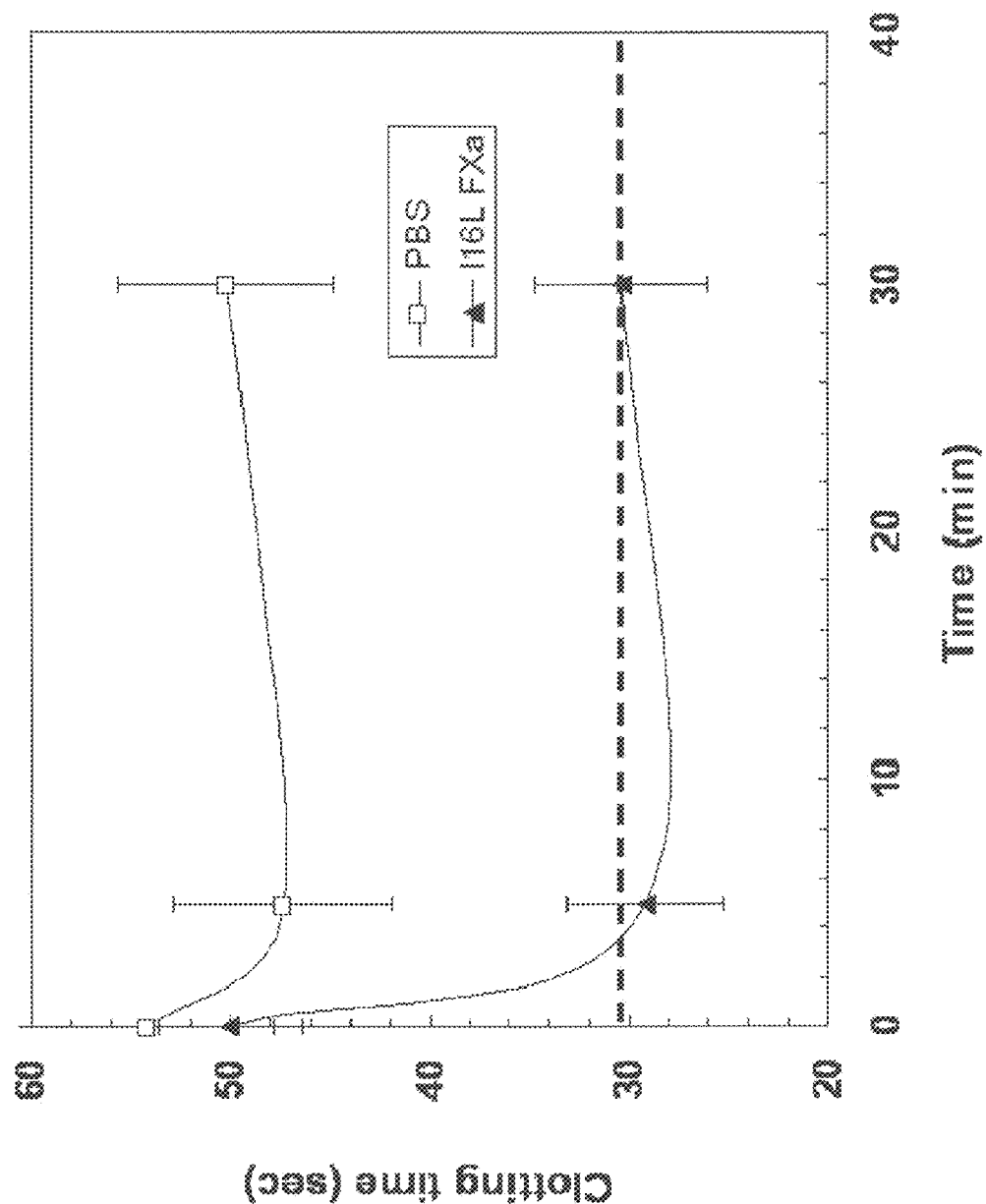
FIG. 7. Correction of the aPTT. Factor Xa-116L (200 μg/kg; n=7 mice) or PBS (n=4 mice) were injected into hemophilia B mice (C57BL/6) via the tail vein. At 5 and 30 min post-injection, blood was collected and an aPTT assay was performed. The red dotted line represents the aPTT value of normal C57B1/6 animals.

We next evaluated the ability of zymogen-like FXaI16L (FXaI235L) to modulate hemostasis in a murine model of hemophilia (Schlachterman, et. al., 2005, J. Thromb. Haemost., 3, 2730-2737). The aPTT value of hemophilia B mice (C57BL/6) is approximately 50-55 sec. Factor XaI16L (200 µg/kg; n=7) or PBS (n=4) were injected via the tail vein of hemophilia B mice. At selected time points (5 and 30 min) blood was collected and an aPTT was performed on all samples. As shown in FIG. 7, infusion of FXaI16L (FXaI235L) resulted in complete correction of the aPTT to levels seen in normal animals. This effect was sustained for at least 30 min indicating that the molecule has a relatively long half life in vivo. Infusion of PBS had only a marginal effect. These data are consistent with the in vitro plasma experiments above and indicate that indeed FXaI16L (FXaI235L) and possibly other zymogen-like FXa variants can effectively modulate hemostasis in vivo.

Figure 8:
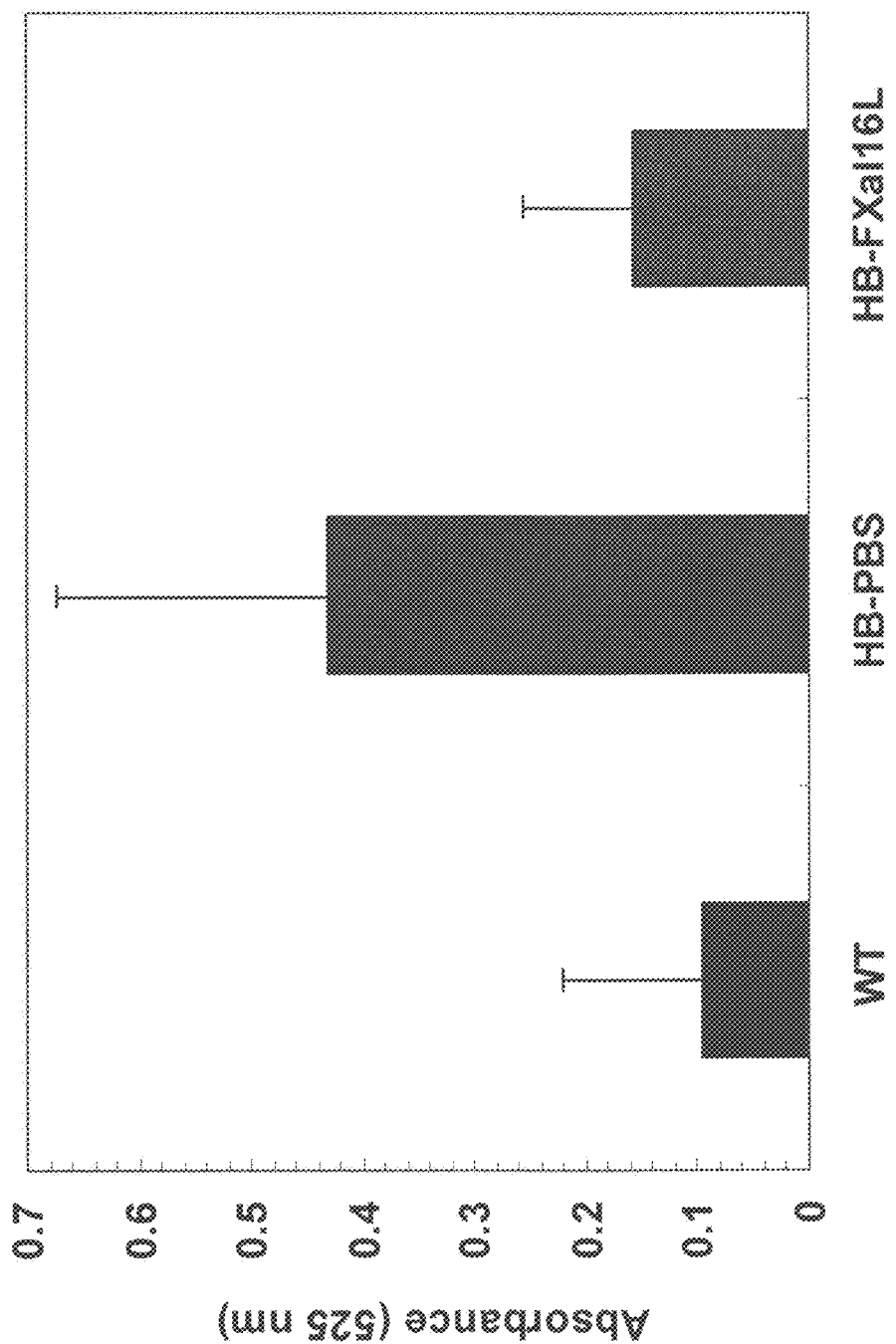
FIG. 8. Hemostatic assessment following tail-clip assay in hemophilia B mice. Blood loss is measured by the hemoglobin content of the saline solution by A525 post-injury. The number of mice (Balb c) are; wild-type (n=7); HB-PBS (n=6); and HB-FXaI16L (n=7).

To further test the effectiveness of FXaI16L (FXaI235L) in vivo, we examined whether this molecule could correct the bleeding time of hemophilia B mice following injury to the tail (Schlachterman, et. al., 2005, J. Thromb. Haemost., 3, 2730-2737). Blood loss was measured during a 10-min period after sectioning the distal part of the tail. In this type of assay, blood loss is minimal in normal wild-type Balb-c mice (n=7) and quite substantial in PBS injected (n=6) hemophilia B mice (Balb c) following the tail injury (FIG. 8). In contrast, injection of 450 µg/kg of FXaI16L (FXaI235L) significantly reduced the total amount of blood loss following tail injury (n=7). Taken together these data provide evidence that FXaI16L has the ability to improve hemostasis in hemophilia A or B patients.

REFERENCES

1. Furie, B. and Furie, B. C. (1976) Spectral changes in bovine factor X associated with activation by the venom coagulant protein Vipera russelli. *J. Biol. Chem.* 251, 6807-6814.
2. Robison, D., Furie, B., Furie, B. C., and Bing, D. H. (1980) Active site of bovine factor X. Characterization using substituted benzamidines as competitive inhibitors and affinity-labeling reagents. *J. Biol. Chem.* 255, 2014-2021.
3. Keyt, B., Furie, B. C., and Furie, B. (1982) Structural transitions in bovine factor X associated with metal binding and zymogen activation. Studies using conformational-specific antibodies. *J. Biol. Chem.* 257, 8687-8695.
4. Persson, E., Valcarce, C., and Stenflo, J. (1991) The γ-carboxyglutamic acid and epidermal growth factor-like domains of factor X. Effect of isolated domains on prothrombin activation and endothelial cell binding of factor X. *J Biol Chem* 266, 2458.
5. Persson, E., Hogg, P. J., and Stenflo, J. (1993) Effects of $Ca^{2+}$ binding on the protease module of factor Xa and its interaction with factor Va: evidence for two Gla-independent $Ca^{2+}$ binding sites in factor Xa. *J Biol Chem* 268, 22531-22539.
6. Dahlbäck, B. and Stenflo, J. (1978) Binding of bovine coagulation factor Xa to platelets. *Biochemistry* 17, 4938-4945.
7. Miletich, J. P., Jackson, C. M., and Majerus, P. W. (1978) Properties of the factor Xa binding site on human platelets. *J. Biol. Chem.* 253, 6908-6916.
8. Madison, E., Kobe, A., Gething, M., Sambrook, J. F., and Goldsmith, E. (1993) Converting tissue plasminogen activator to a zymogen: A regulatory triad of Asp-His-Ser. *Science* 262, 419-421.
9. Tachias, K. and Madison, E. (1996) Converting tissue-type plasminogen activator into a zymogen. *J. Biol. Chem.* 271, 28749-28752.
10. Tachias, K. and Madison, E. (1997) Converting tissue type plasminogen activator into a zymogen. Important role of Lys156 *J. Biol. Chem.* 272, 28-31.
11. Renatus, M., Engh, R. A., Stubbs, M. T., Huber, R., Fischer, S., Kohnert, U., and Bode, W. (1997) Lysine 156 promotes the anomalous proenzyme activity of tPA: X-ray crystal structure of single-chain human tPA. *EMBO J.* 16, 4797-4805.
12. Eigenbrot, C., Kirchhofer, D., Dennis, M. S., Santell, L., Lazarus, R. A., Stamos, J., and Ultsch M H (2001) The factor VII zymogen structure reveals reregistration of beta strands during activation. *Structure* 9, 627-636.
13. Venkateswarlu, D., Perera, L., Darden, T., and Pedersen, L. G. (2002) Structure and dynamics of zymogen human blood coagulation factor X. *Biophys. J.* 82, 1190-1206.
14. Camire, R. M. Prothrombinase assembly and S1 site occupation restore the catalytic activity of FXa impaired by mutation at the sodium-binding site. (2002) *J. Biol. Chem.* 277, 37863-37870.
15. Rezaie, A. R., Neuenschwander, P. F., Morrissey, J. H., and Esmon, C. T. (1993) Analysis of the functions of the first epidermal growth factor-like domain of factor X. *J Biol Chem* 268, 8176-8180.
16. Rezaie, A. R. and Esmon, C. T. (1994) Asp-70 to Lys mutant of factor X lacks high affinity Ca2+ binding site yet retains function. *J. Biol. Chem.* 269, 21495-21499.

17. Rezaie, A. R. and Esmon, C. T. (1995) Contribution of residue 192 in factor Xa to enzyme specificity and function. *J. Biol. Chem.* 270, 16176-16181.
18. Rezaie, A. R. (1996) Role of residue 99 at the S2 subsite of factor Xa and activated protein C in enzyme specificity. *J. Biol. Chem.* 271, 23807-23814.
19. Rezaie, A. R. (2000) Identification of basic residues in the heparin-binding exosite of factor Xa critical for heparin and factor Va binding. *J. Biol. Chem.* 275, 3320-3327.
20. Rezaie, A. R. and He, X. (2000) Sodium binding site of factor Xa: Role of sodium in the prothrombinase complex. *Biochemistry* 39, 1817-1825.
21. Larson, P. J., Camire, R. M., Wong, D., Fasano, N. C., Monroe, D. M., Tracy, P. B., and High, K. A. (1998) Structure/function analyses of recombinant variants of human factor Xa: Factor Xa incorporation into prothrombinase on the activated platelet surface is not mimicked by synthetic phospholipid vesicles. *Biochemistry* 37, 5029-5038.
22. Stanley, T. B., Jin, D. Y., Lin, P., and Stafford, D. W. (1999) The propeptides of the vitamin K-dependent proteins possess different affinities for the vitamin K-dependent carboxylase. *J. Biol. Chem.* 274, 16940-16944.
23. Stanley, T. B., Humphries, J., High, K. A., and Stafford, D. W. (1999) Amino acids responsible for the reduced affinities of vitamin K-dependent propeptides for the carboxylase. *Biochemistry* 38, 15681-15687.
24. Camire, R. M., Larson, P. J., Stafford, D. W., and High, K. A. (2000) Enhanced γ-carboxylation of recombinant factor X using a chimeric construct containing the prothrombin propeptide. *Biochemistry* 39, 14322-14329.
25. Zhong, D., Bajaj, M. S., Schmidt, A. E., and Bajaj, S. P. (2001) The N-terminal EGF-like domain in factor IX and factor X represents an important recognition motif for binding to tissue factor. *J. Biol. Chem.* 277, 3622-3631.
26. Chase, T. and Shaw, E. (1969) Comparison of the esterase activities of trypsin, plasmin, and thrombin on guanidinobenzoate esters. Titration of the enzymes. *Biochemistry.* 8, 2212-2224.
27. Bock, P. E., Craig, P. A., Olson, S. T., and Singh, P. (1989) Isolation of human blood coagulation α-factor Xa by soybean-trypsin inhibitor-Sepharose chromatography and its active-site titration with fluorescein mono-r-guanidinobenzoate. *Arch. Bioch. Biophys.* 273, 375-388.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated Factor Xa variant in which the Val corresponding to position 236 of SEQ ID NO:1 is substituted with Ala.

2. An isolated Factor Xa variant comprising amino acids 41-179 and amino acids 235-488 of SEQ ID NO:1, wherein the Val corresponding to position 236 of SEQ ID NO:1 is substituted with Ala.

3. An isolated Factor Xa variant consisting essentially of amino acids 41-179 and amino acids 235-488 of SEQ ID NO:1, wherein the Val corresponding to position 236 of SEQ ID NO:1 is substituted with Ala.

4. A pharmaceutical composition comprising the Factor Xa variant of claim 1 in a biologically compatible carrier.

5. A pharmaceutical composition comprising the Factor Xa variant of claim 2 in a biologically compatible carrier.

6. A pharmaceutical composition comprising the Factor Xa variant of claim 3 in a biologically compatible carrier.

7. A method for treatment of a hemostasis related disorder in a patient in need thereof comprising administration of a therapeutically effective amount of the Factor Xa variant of claim 1 in a biologically acceptable carrier.

8. A method for treatment of a hemostasis related disorder in a patient in need thereof comprising administration of a therapeutically effective amount of the Factor Xa variant of claim 2 in a biologically acceptable carrier.

9. A method for treatment of a hemostasis related disorder in a patient in need thereof comprising administration of a therapeutically effective amount of the Factor Xa variant of claim 3 in a biologically acceptable carrier.

10. The method of claim 7, wherein said disorder is selected from the group consisting of hemophilia A and B, hemophilia A and B associated with inhibitory antibodies, coagulation factor deficiency, vitamin K epoxide reductase C1 deficiency, gamma-carboxylase deficiency, bleeding associated with trauma, injury, thrombosis, thrombocytopenia, stroke, coagulopathy, disseminated intravascular coagulation (DIC), over-anticoagulation treatment disorders, Bernard Soulier syndrome, Glanzmann thrombasthenia, and storage pool deficiency.

11. The method of claim 10, wherein the deficient coagulation factor is selected from the group consisting of at least one of factor VII, factor IX, factor X, factor XI, factor V, factor XII, factor II, and von Willebrand factor.

12. The method of claim 10, wherein said disorder is Hemophilia A.

13. The method of claim 10, wherein said disorder is Hemophilia B.

14. The method of claim 10, wherein said disorder is stroke.

15. The method of claim 10, wherein said disorder is Glanzmann thrombasthenia.

16. The method of claim 10, wherein said over-anticoagulation treatment disorder results from administration of heparin, low molecular weight heparin, pentasaccharide, warfarin, small molecule antithrombotics and FXa inhibitors.

17. The method of claim 16, wherein said over-anticoagulation treatment disorder results from administration of a FXa inhibitor.

18. The method of claim 7, wherein said Factor Xa variant is administered intravenously at least once a day at a dosage between about 10 and 500 µg/kg.

19. The method of claim 7, wherein said Factor Xa variant is administered intravenously at least once a day at a dosage between about 10 and 250 µg/kg.

20. The method of claim 7, wherein said Factor Xa variant is encapsulated in a liposome or mixed with phospholipids or micelles.

* * * * *

SEQUENCE LISTING

```
<160> NUMBER OF SEQ ID NOS: 6

<210> SEQ ID NO 1
<211> LENGTH: 488
<212> TYPE: PRT
<213> ORGANISM: Artificial Sequence
<220> FEATURE:
<223> OTHER INFORMATION: Synthetic Sequence

<400> SEQUENCE: 1

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Arg Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190
```

```
Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485

<210> SEQ ID NO 2
<211> LENGTH: 1467
<212> TYPE: DNA
<213> ORGANISM: Artificial Sequence
<220> FEATURE:
<223> OTHER INFORMATION: Synthetic Sequence

<400> SEQUENCE: 2
atggggcgcc cactgcacct cgtcctgctc agtgcctccc tggctggcct cctgctgctc      60
ggggaaagtc tgttcatccg cagggagcag gccaacaaca tcctggcgag ggtcaggagg     120
gccaattcct ttcttgaaga gatgaagaaa ggacacctcg aaagagagtg catggaagag     180
acctgctcat acgaagaggc ccgcgaggtc tttgaggaca gcgacaagac gaatgaattc     240
tggaataaat acaagatgg cgaccagtgt gagaccagtc cttgccagaa ccagggcaaa     300
tgtaaagacg gcctcgggga atacacctgc acctgtttag aaggattcga aggcaaaaac     360
```

-continued

```
tgtgaattat tcacacggaa gctctgcagc ctggacaacg gggactgtga ccagttctgc    420
cacgaggaac agaactctgt ggtgtgctcc tgcgcccgcg ggtacaccct ggctgacaac    480
ggcaaggcct gcattccac agggccctac ccctgtggga acagaccct ggaacgcagg     540 aagaggtcag tggcccaggc caccagcagc agcggggagg cccctgacag catcacatgg    600
aagccatatg atgcagccga cctggacccc accgagaacc ccttcgacct gcttgacttc    660
aaccagacgc agcctgagag gggcgacaac aacctcacgc gtatcgtggg aggccaggaa    720
tgcaaggacg gggagtgtcc ctggcaggcc ctgctcatca atgaggaaaa cgagggtttc    780
tgtggtggaa ctattctgag cgagttctac atcctaacgg cagcccactg tctctaccaa    840
gccaagagat tcaaggtgag ggtaggtgac cggaacacgg agcaggagga gggcggtgag    900
gcggtgcacg aggtggaggt ggtcatcaag cacaaccggt tcacaaagga gacctatgac    960
ttcgacatcg ccgtgctccg gctcaagacc cccatcacct tccgcatgaa cgtggcgcct   1020
gcctgcctcc ccgagcgtga ctgggccgag tccacgctga tgacgcagaa gacggggatt   1080
gtgagcggct cgggcgcac ccacgagaag gccggcagt ccaccaggct caagatgctg     1140
gaggtgccct acgtggaccg caacagctgc aagctgtcca gcagcttcat catcacccag   1200
aacatgttct gtgccggcta cgacaccaag caggaggatg cctgccaggg ggacagcggg   1260
ggcccgcacg tcacccgctt caaggacacc tacttcgtga caggcatcgt cagctgggga   1320
gagggctgtg cccgtaaggg gaagtacggg atctacacca aggtcaccgc cttcctcaag   1380
tggatcgaca ggtccatgaa aaccagggc ttgcccaagg ccaagagcca tgccccggag    1440
gtcataacgt cctctccatt aaagtga                                      1467
```

```
<210> SEQ ID NO 3
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 3

Arg Lys Arg Arg Lys Arg
 1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 4

Ile Val Gly Gly
 1

<210> SEQ ID NO 5
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 5

Ala Asn Ser Phe
 1
```

```
<210> SEQ ID NO 6
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 6

Thr Leu Glu Arg
 1
```